(12) United States Patent
Bender et al.

(10) Patent No.: US 7,814,731 B2
(45) Date of Patent: Oct. 19, 2010

(54) AUTOMATED DRUG PREPARATION APPARATUS INCLUDING A BLUETOOTH COMMUNICATIONS NETWORK

(75) Inventors: Jayson Lee Bender, Ormond Beach, FL (US); Michael J. Kenney, Ormond Beach, FL (US); Abdul Wahid Khan, Lindenhurst, IL (US); G. Rodney Wolford, Port Orange, FL (US)

(73) Assignee: Forhealth Technologies, Inc., Daytona Beach, FL (US)

( * ) Notice: Subject to any disclaimer, the term of this patent is extended or adjusted under 35 U.S.C. 154(b) by 1002 days.

(21) Appl. No.: 11/551,555

(22) Filed: Oct. 20, 2006

(65) Prior Publication Data
US 2008/0169046 A1     Jul. 17, 2008

(51) Int. Cl.
*B65B 5/06* (2006.01)
(52) U.S. Cl. .................... 53/467; 53/276; 700/117
(58) Field of Classification Search ............ 53/467, 53/469, 477, 240, 267, 373.7; 700/117, 795
See application file for complete search history.

(56) References Cited

U.S. PATENT DOCUMENTS

| | | | |
|---|---|---|---|
| 2,005,020 A | 6/1935 | Bossert | |
| 2,560,728 A | 7/1951 | Lee | |
| 2,627,470 A | 2/1953 | Seiferth | |
| 2,880,723 A | 4/1959 | Adams | |
| 2,981,432 A | 4/1961 | Flood | |
| 2,988,984 A | 6/1961 | Eckert | |
| 3,200,486 A | 8/1965 | Shields | |
| 3,527,017 A | 9/1970 | Taylor et al. | |
| 3,651,615 A | 3/1972 | Bohner et al. | |
| 3,676,271 A | 7/1972 | Hake et al. | |
| 3,736,933 A | 6/1973 | Szabo | |
| 3,807,467 A | 4/1974 | Tascher et al. | |
| 3,823,818 A | 7/1974 | Shaw | |
| 3,835,897 A | 9/1974 | Gess | |
| 3,848,485 A | 11/1974 | Grenci | |
| 3,865,236 A | 2/1975 | Rycroft | |
| 3,878,026 A | 4/1975 | Snyder et al. | |
| 3,880,211 A | 4/1975 | Gess | |
| 3,898,861 A | 8/1975 | McMillin | |
| 3,935,883 A | 2/1976 | Stach et al. | |
| 3,965,945 A | 6/1976 | Ross | |
| 4,058,121 A | 11/1977 | Choksi et al. | |

(Continued)

OTHER PUBLICATIONS

U.S. Appl. No. 11/434,850.
U.S. Appl. No. 11/466,354.

*Primary Examiner*—Paul R Durand
(74) *Attorney, Agent, or Firm*—Leason Ellis LLP

(57) ABSTRACT

An automated medication preparation system for preparing a prescribed dosage of medication in a drug delivery device includes a plurality of stations for receiving, handling and processing the drug delivery device so that the prescribed dosage of medication is delivered to the drug delivery device. At least one of the stations includes a peripheral device for performing at least one operation and a transporting device that receives and holds more than one drug delivery device and moves the drug delivery devices in a controlled manner from one station to another station. The system includes a master controller that tracks and controls the movement of the transporting device and operation of equipment at one or more stations. In addition, a system further includes a Bluetooth communications network between the peripheral device and the master controller such that that the peripheral device automatically communicates with the controller when the peripheral device is within a predetermined distance from the controller.

12 Claims, 17 Drawing Sheets

U.S. PATENT DOCUMENTS

| | | |
|---|---|---|
| 4,195,526 A | 4/1980 | Amos et al. |
| 4,472,357 A | 9/1984 | Levy et al. |
| 4,501,306 A | 2/1985 | Chu et al. |
| 4,502,616 A | 3/1985 | Meierhoefer |
| 4,512,472 A | 4/1985 | Jarund et al. |
| 4,512,475 A | 4/1985 | Federighi et al. |
| 4,535,820 A | 8/1985 | Raines |
| 4,546,901 A | 10/1985 | Buttarazzi |
| 4,586,546 A | 5/1986 | Mezei et al. |
| 4,624,148 A | 11/1986 | Averette |
| 4,639,250 A | 1/1987 | Rycroft |
| 4,674,652 A | 6/1987 | Aten et al. |
| 4,683,916 A | 8/1987 | Raines |
| 4,699,186 A | 10/1987 | Palin et al. |
| 4,702,788 A | 10/1987 | Okui et al. |
| 4,758,230 A | 7/1988 | Rycroft |
| 4,773,285 A | 9/1988 | Dionne et al. |
| 4,823,982 A | 4/1989 | Aten et al. |
| 4,854,355 A | 8/1989 | Chazot et al. |
| 4,861,335 A | 8/1989 | Reynolds et al. |
| 4,865,592 A | 9/1989 | Rycroft |
| 4,944,736 A | 7/1990 | Holtz |
| 4,974,617 A | 12/1990 | Simon et al. |
| 5,004,962 A | 4/1991 | Fonss et al. |
| 5,012,845 A | 5/1991 | Averette |
| 5,019,048 A | 5/1991 | Margolin |
| 5,040,437 A | 8/1991 | Mueller |
| 5,082,502 A | 1/1992 | Lee et al. |
| 5,124,434 A | 6/1992 | O'Brien |
| 5,125,748 A | 6/1992 | Bjornson et al. |
| 5,178,684 A | 1/1993 | Hutchins, Sr. |
| 5,188,696 A | 2/1993 | Good, Jr. |
| 5,208,762 A | 5/1993 | Charhut et al. |
| 5,229,074 A | 7/1993 | Heath et al. |
| 5,256,154 A | 10/1993 | Liebert et al. |
| 5,288,285 A | 2/1994 | Carter |
| 5,309,959 A | 5/1994 | Shaw et al. |
| 5,337,636 A | 8/1994 | Shea |
| 5,337,919 A | 8/1994 | Spaulding et al. |
| 5,341,854 A | 8/1994 | Zezulka et al. |
| 5,356,393 A | 10/1994 | Haber et al. |
| 5,363,885 A | 11/1994 | McConnell et al. |
| 5,380,296 A | 1/1995 | Smedley et al. |
| 5,431,201 A | 7/1995 | Torchia et al. |
| 5,431,299 A | 7/1995 | Brewer et al. |
| 5,451,528 A | 9/1995 | Raymoure et al. |
| 5,453,246 A | 9/1995 | Nakayama et al. |
| 5,479,969 A | 1/1996 | Hardie et al. |
| 5,496,288 A | 3/1996 | Sweeney |
| 5,511,594 A | 4/1996 | Brennan et al. |
| 5,542,935 A | 8/1996 | Unger et al. |
| 5,593,267 A | 1/1997 | McDonald et al. |
| 5,597,530 A | 1/1997 | Smith et al. |
| 5,611,430 A | 3/1997 | Albrecht et al. |
| 5,647,409 A | 7/1997 | Christ et al. |
| 5,651,775 A | 7/1997 | Walker et al. |
| 5,669,599 A | 9/1997 | Toh et al. |
| 5,704,921 A | 1/1998 | Carilli |
| 5,735,181 A | 4/1998 | Anderson |
| 5,753,451 A | 5/1998 | Smith |
| 5,755,894 A | 5/1998 | Bowman et al. |
| 5,769,086 A | 6/1998 | Ritchart et al. |
| 5,782,157 A | 7/1998 | Ellington et al. |
| 5,805,454 A | 9/1998 | Valerino, Sr. et al. |
| 5,819,050 A * | 10/1998 | Boehling et al. ............ 710/104 |
| 5,826,409 A | 10/1998 | Slepicka et al. |
| 5,855,839 A | 1/1999 | Brunel et al. |
| 5,883,370 A | 3/1999 | Walker et al. |
| 5,884,457 A | 3/1999 | Ortiz et al. |
| 5,887,722 A | 3/1999 | Albrecht et al. |
| 5,893,259 A | 4/1999 | Posge |
| 5,899,889 A | 5/1999 | Futagawa et al. |
| 5,900,557 A | 5/1999 | Tanihata et al. |
| 5,911,252 A | 6/1999 | Cassel |
| 5,915,089 A | 6/1999 | Stevens et al. |
| 5,948,360 A | 9/1999 | Rao et al. |
| 5,985,038 A | 11/1999 | Dawson et al. |
| 6,027,472 A | 2/2000 | Kriesel et al. |
| 6,033,911 A | 3/2000 | Schultz et al. |
| 6,048,086 A | 4/2000 | Valerino, Sr. |
| 6,068,614 A | 5/2000 | Kimber et al. |
| 6,142,039 A | 11/2000 | Herring, Sr. |
| 6,200,289 B1 | 3/2001 | Hochman et al. |
| 6,202,923 B1 | 3/2001 | Boyer et al. |
| 6,226,745 B1 | 5/2001 | Wiederhold |
| 6,240,952 B1 | 6/2001 | Schroeder |
| 6,343,690 B1 | 2/2002 | Britton et al. |
| 6,360,794 B1 | 3/2002 | Turner |
| 6,370,841 B1 * | 4/2002 | Chudy et al. .................. 53/411 |
| 6,599,476 B1 | 7/2003 | Watson et al. |
| 6,604,903 B2 | 8/2003 | Osborne et al. |
| 6,615,881 B2 | 9/2003 | Bartholomew et al. |
| 6,616,771 B2 | 9/2003 | Osborne et al. |
| 6,623,455 B2 | 9/2003 | Small et al. |
| 6,715,265 B2 * | 4/2004 | Franzaroli .................... 53/435 |
| 6,722,404 B2 | 4/2004 | Osborne |
| 6,813,868 B2 | 11/2004 | Baldwin et al. |
| 6,877,530 B2 | 4/2005 | Osborne et al. |
| 6,915,823 B2 | 7/2005 | Osborne et al. |
| 6,986,234 B2 | 1/2006 | Liedtke |
| 6,991,002 B2 | 1/2006 | Osborne et al. |
| 7,007,443 B2 | 3/2006 | Liedtke et al. |
| 7,017,622 B2 | 3/2006 | Osborne et al. |
| 7,017,623 B2 | 3/2006 | Tribble et al. |
| 7,025,098 B2 | 4/2006 | Osborne |
| 7,096,212 B2 | 8/2006 | Tribble et al. |
| 2001/0018937 A1 | 9/2001 | Nemoto |
| 2002/0020459 A1 | 2/2002 | Baldwin et al. |
| 2002/0092275 A1 * | 7/2002 | Kim ........................... 53/493 |
| 2002/0188467 A1 | 12/2002 | Eke |
| 2002/0198738 A1 | 12/2002 | Osborne |
| 2003/0033532 A1 | 2/2003 | Marks |
| 2003/0036744 A1 * | 2/2003 | Struys et al. ................. 604/503 |
| 2003/0114109 A1 * | 6/2003 | Thayer et al. ................. 455/66 |
| 2003/0195934 A1 * | 10/2003 | Peterson et al. ............. 709/206 |
| 2004/0001906 A1 | 1/2004 | Carhuff et al. |
| 2004/0088187 A1 | 5/2004 | Chudy et al. |
| 2004/0088951 A1 * | 5/2004 | Baldwin et al. ............... 53/425 |
| 2004/0159078 A1 * | 8/2004 | Rice et al. .................... 53/445 |
| 2004/0236630 A1 | 11/2004 | Kost et al. |
| 2004/0250842 A1 | 12/2004 | Adams et al. |
| 2005/0007249 A1 * | 1/2005 | Eryurek et al. .............. 340/511 |
| 2005/0045242 A1 | 3/2005 | Osborne |
| 2005/0113969 A1 * | 5/2005 | Spano et al. ................. 700/237 |
| 2005/0145644 A1 * | 7/2005 | Mori et al. .................. 221/242 |
| 2005/0203482 A1 * | 9/2005 | Chinea ....................... 604/500 |
| 2005/0224137 A1 | 10/2005 | Tribble et al. |
| 2005/0228536 A1 * | 10/2005 | Mohr et al. ................. 700/237 |
| 2005/0240289 A1 * | 10/2005 | Hoyte et al. .................. 700/49 |
| 2005/0252572 A1 | 11/2005 | Khan et al. |
| 2005/0257497 A1 * | 11/2005 | Kim ......................... 53/131.5 |
| 2006/0107623 A1 * | 5/2006 | Rice et al. .................... 53/494 |
| 2006/0167967 A1 * | 7/2006 | Defosse ...................... 709/201 |
| 2006/0178578 A1 | 8/2006 | Tribble et al. |
| 2007/0033903 A1 * | 2/2007 | Gertitschke et al. ............ 53/77 |
| 2007/0062156 A1 * | 3/2007 | Kim ......................... 53/131.5 |

* cited by examiner

FIG. 15
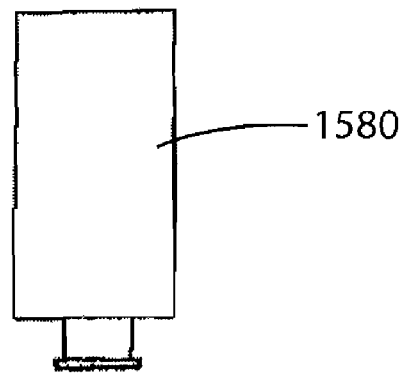
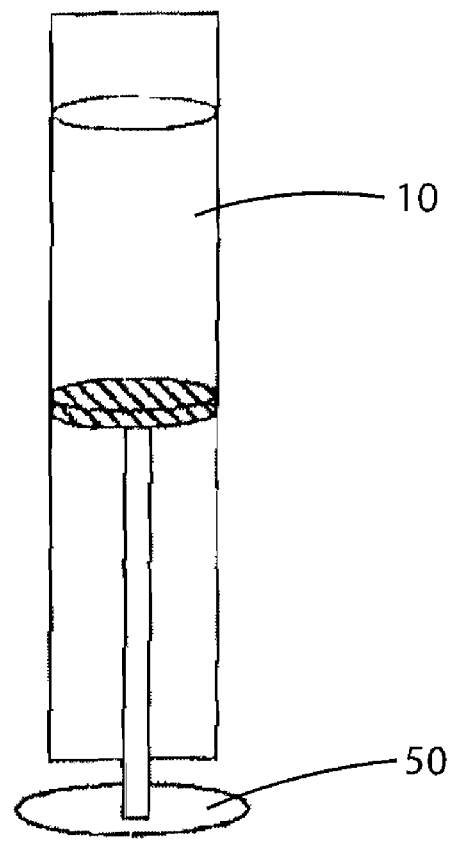

AUTOMATED DRUG PREPARATION APPARATUS INCLUDING A BLUETOOTH COMMUNICATIONS NETWORK

TECHNICAL FIELD

The present invention relates generally to medical and pharmaceutical equipment, and more particularly, to an automated system for preparing a drug delivery device, such as a syringe, to receive a unit dose of medication and then dispensing the unit dose of medication into the drug delivery device (e.g., a syringe) and to a number of safety and control features that preserve the integrity and optimize the performance and capabilities of the system.

BACKGROUND

Disposable syringes are in widespread use for a number of different types of applications. For example, syringes are used not only to withdraw a fluid (e.g., blood) from a patient but also to administer a medication to a patient. In the latter, a cap or the like is removed from the syringe and a unit dose of the medication is carefully measured and then injected or otherwise disposed within the syringe.

As technology advances, more and more sophisticated, automated systems are being developed for preparing and delivering medications by integrating a number of different stations, with one or more specific tasks being performed at each station. For example, one type of exemplary automated system operates as a syringe filling apparatus that receives user inputted information, such as the type of medication, the volume of the medication and any mixing instructions, etc. The system then uses this inputted information to disperse the correct medication into the syringe up to the inputted volume.

In some instances, the medication that is to be delivered to the patient includes more than one pharmaceutical substance. For example, the medication can be a mixture of several components, such as several pharmaceutical substances.

By automating the medication preparation process, increased production and efficiency are achieved. This results in reduced production costs and also permits the system to operate over any time period of a given day with only limited operator intervention for manual inspection to ensure proper operation is being achieved. Such a system finds particular utility in settings, such as large hospitals, including a large number of doses of medications that must be prepared daily. Traditionally, these doses have been prepared manually in what is an exacting but tedious responsibility for a highly skilled staff. In order to be valuable, automated systems must maintain the exacting standards set by medical regulatory organizations, while at the same time simplifying the overall process and reducing the time necessary for preparing the medications.

Because syringes are used often as the carrier means for transporting and delivering the medication to the patient, it is advantageous for these automated systems to be tailored to accept syringes. However, the previous methods of dispersing the medication from the vial and into the syringe were very time consuming and labor intensive. More specifically, medications and the like are typically stored in a vial that is sealed with a safety cap or the like. In conventional medication preparation, a trained person retrieves the correct vial from a storage cabinet or the like, confirms the contents and then removes the safety cap manually. This is typically done by simply popping the safety cap off with one's hands. Once the safety cap is removed, the trained person inspects the integrity of the membrane and cleans the membrane. An instrument, e.g., a needle, is then used to pierce the membrane and withdraw the medication contained in the vial. The withdrawn medication is then placed into a syringe to permit subsequent administration of the medication from the syringe.

If the medication needs to be reconstituted, the medication initially comes in a solid form and is contained in an injectable drug vial and then the proper amount of diluent is added and the vial is agitated to ensure that all of the solid goes into solution, thereby providing a medication having the desired concentration. The drug vial is typically stored in a drug cabinet or the like and is then delivered to other stations where it is processed to receive the diluent.

What is needed in the art and has heretofore not been available is a system and method for automating the medication preparation process and more specifically, an automated system and method for preparing a syringe including the filling of medication therein, as well as a number of safety and communication features and user interfaces that improve the safety and proficiency of the process.

SUMMARY

An automated medication preparation system for preparing a prescribed dosage of medication in a drug delivery device includes a plurality of stations for receiving, handling and processing the drug delivery device so that the prescribed dosage of medication is delivered to the drug delivery device. At least one of the stations includes a peripheral device for performing at least one operation and a transporting device that receives and holds more than one drug delivery device and moves the drug delivery devices in a controlled manner from one station to another station. The system includes a master controller that tracks and controls the movement of the transporting device and operation of equipment at one or more stations.

In addition, a system further includes a Bluetooth communications network between the peripheral device and the master controller such that that the peripheral device automatically communicates with the controller when the peripheral device is within a predetermined distance from the controller. The system is configured so that two or more separate drug delivery devices are acted upon at the same time at two or more different stations.

A method of operating an automated medication preparation system to prepare and deliver a prescribed dosage of medication to a drug delivery device includes the steps of: (1) inputting a drug order that contains instructions for forming the prescribed dosage of medication; (2) providing a plurality of stations for receiving, handling and processing a drug delivery device so that the prescribed dosage of medication is delivered to the drug delivery device, wherein at least one of the stations includes a peripheral device for performing at least one operation; (3) operating a transporting device that receives and holds more than one drug delivery device such that each drug delivery device moves in a controlled manner from one station to another station; (4) communicating with the peripheral device by means of a Bluetooth communications network to monitor a status of the at least one operation performed at the peripheral device; and (5) delivering, in an automated manner, the prescribed dosage of medication to the drug delivery device in conformity with the drug order.

Further aspects and features of the exemplary automated drug preparation system disclosed herein can be appreciated from the appended Figures and accompanying written description.

BRIEF DESCRIPTION OF THE DRAWINGS

FIG. 12A is a side cross-sectional view of laser assembly for determine a liquid volume in a syringe or the like;

FIG. 15 is a side cross-sectional view of an apparatus for measuring fluid level with a camera;

DETAILED DESCRIPTION OF PREFERRED EMBODIMENTS

Figure 1:
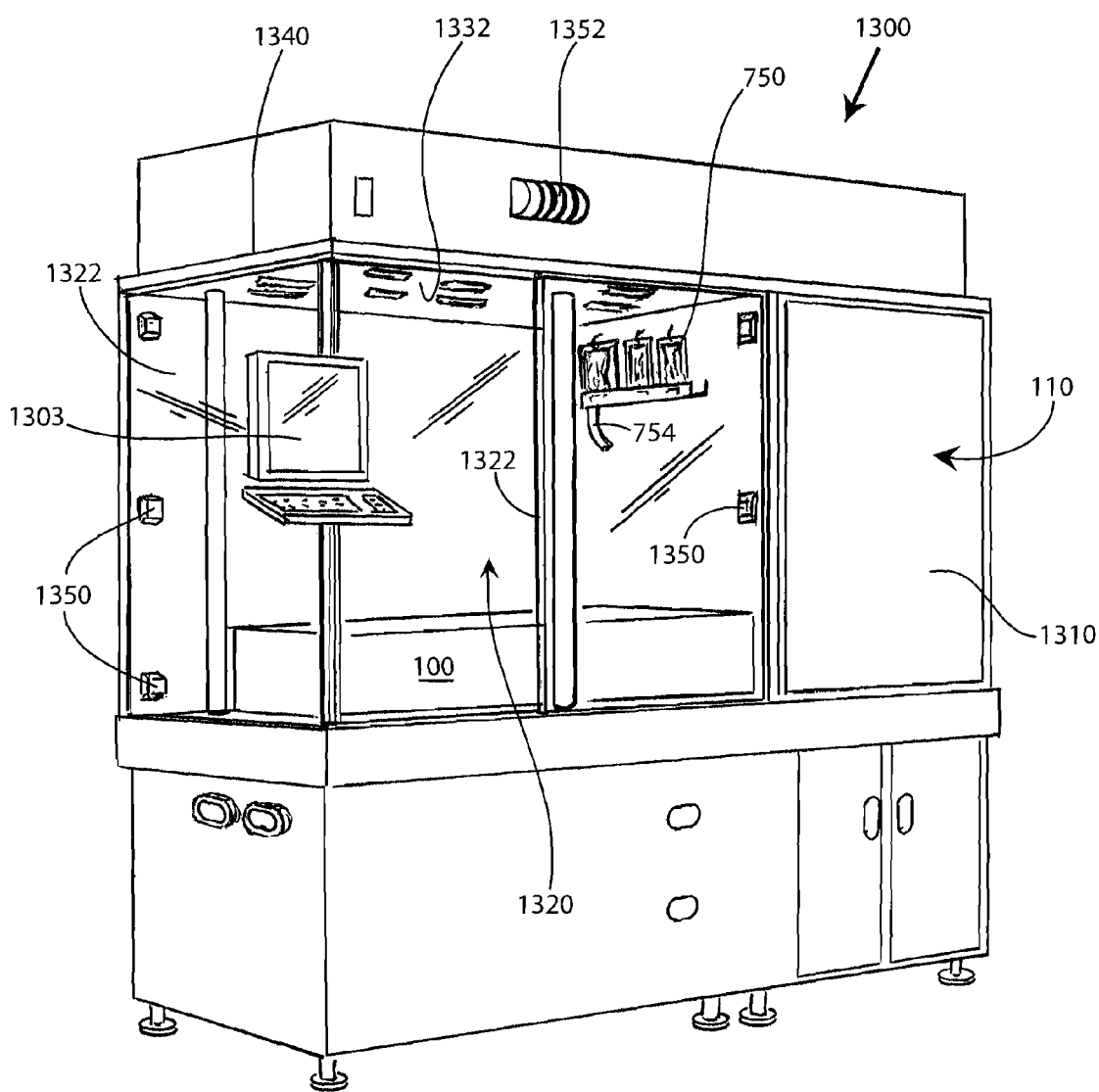
FIG. 1 is a perspective view of a housing that contains an automated drug delivery system that prepares a dosage of medication to be administered to a patient.

FIG. 1 is perspective view of a housing 1300 that is constructed to house an automated drug preparation and delivery system 100 in a sealed, controlled environment when the housing structure is closed (sealed). A user interface, such as a computer, 1303 is provided to permit an operator not only to enter information, such as drug orders, but also to monitor the progress and operation of the system 100. The housing 1300 and its components are described in greater detail below.

Figure 2:
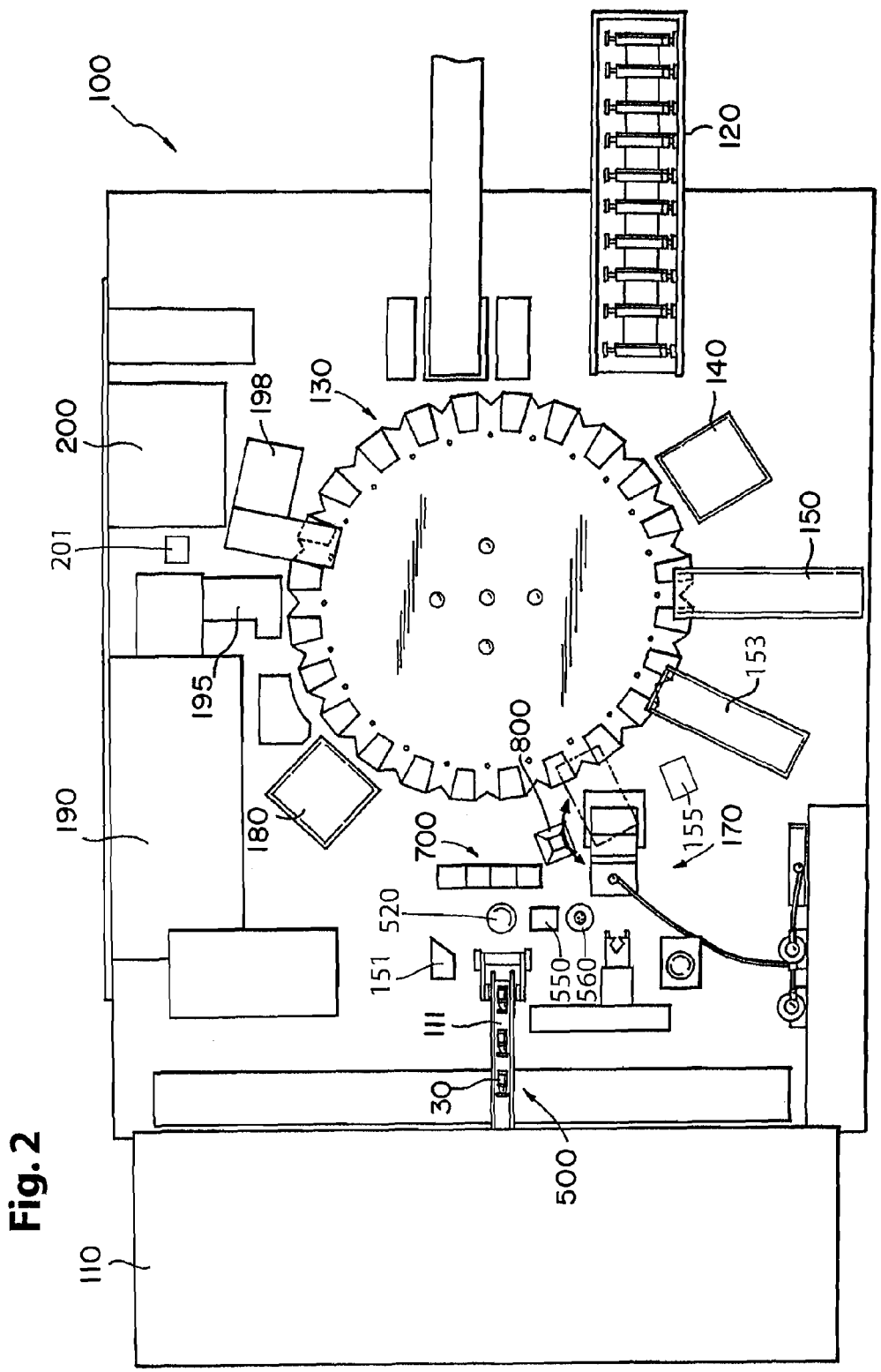
FIG. 2 is a diagrammatic plan view of the automated system for preparing a medication to be administered to a patient.

FIG. 2 is a schematic diagram illustrating one exemplary automated system, generally indicated at 100, for the preparation of a medication. The automated system 100 is divided into a number of stations where a specific task is performed based on the automated system 100 receiving user input instructions, processing these instructions and then preparing unit doses of one or more medications in accordance with the instructions. The automated system 100 includes a station 110 where medications and other substances used in the preparation process are stored. As used herein, the term "medication" refers to a medicinal preparation for administration to a patient. Often, the medication is initially stored as a solid, e.g., a powder, to which a diluent is added to form a medicinal composition. Thus, the station 110 functions as a storage unit for storing one or more medications, etc., under proper storage conditions. Typically, medications and the like are stored in sealed containers, such as vials, that are labeled to clearly indicate the contents of each vial. The vials are typically stored in columns and further, empty vials can be stored in one column. The station 110 includes a mechanism that permits the controlled discharge of a selected drug vial 60.

A first station 120 is a syringe storage station that houses and stores a number of syringes. For example, up to 500 syringes or more can be disposed in the first station 120 for storage and later use. The first station 120 can be in the form of a bin or the like or any other type of structure than can hold a number of syringes. In one exemplary embodiment, the syringes are provided as a bandolier structure that permits the syringes to be fed into the other components of the system 100 using standard delivery techniques, such as a conveyor belt, etc.

The system 100 also includes an apparatus 130 for advancing the fed syringes from and to various stations of the system 100. The apparatus 130 can be a rotary device, as shown, or it can be a linear apparatus, or it can assume some other shape. For purposes of illustration only, the apparatus 130 is discussed and shown as being a rotary device; however, it is not limited to such a configuration and therefore, the present disclosure is not limiting of the scope of the present invention.

A number of the stations are arranged circumferentially around the rotary apparatus 130 so that the syringe is first loaded at the first station 120 and then rotated a predetermined distance to a next station, etc., as the medication preparation process advances. At each station, a different operation is performed with the end result being that a unit dose of medication is delivered to the syringe that is then ready to be administered.

One exemplary type of rotary apparatus 130 is a multiple station cam-indexing dial that is adapted to perform material handling operations. The indexer is configured to have multiple stations positioned thereabout with individual nests for each station position. One syringe is held within one nest using any number of suitable techniques, including opposing spring-loaded fingers that act to clamp the syringe in its respective nest. The indexer permits the rotary apparatus 130 to be advanced at specific intervals.

At a second station 140, the syringes are loaded into one of the nests or the like of the rotary apparatus 130. One syringe is loaded into one nest of the rotary apparatus 130 in which the syringe is securely held in place. The system 100 preferably includes additional mechanisms for preparing the syringe for use, such as removing a tip cap and extending a plunger of the syringe at a third station 150, as described below. At this point, the syringe is ready for use.

The system 100 also preferably includes a reader 151 that is capable of reading a label disposed on the sealed container containing the medication. The label is read using any number of suitable reader/scanner devices 151, such as a bar code reader, etc., so as to confirm that the proper medication has been selected from the storage unit of the station 110. Multiple readers can be employed in the system at various locations to confirm the accuracy of the entire process. Once the system 100 confirms that the sealed container (drug vial 60) that has been selected contains the proper medication, the vial 60 is delivered to a station 550 using an automated mechanism, such a robotic gripping device, as will be described in greater detail. At the station 550, the vial 60 is prepared by removing the safety cap from the sealed container and then cleaning the exposed end of the vial. Preferably, the safety cap is removed on a deck of the automated system 100 having a controlled environment. In this manner, the safety cap is removed just-in-time for use. Exemplary vial cap removal devices are disclosed in U.S. Pat. No. 6,604,903, which is hereby expressly incorporated by reference in its entirety. In addition, the vial cap can be removed by other devices, such as one which has a member with suction (vacuum) capabilities incorporated therein for removing the cap. In this embodiment, the suction member is applied to the vial cap and then the suction is activated and then the robotic arm that is gripping and hold the vial body itself is twisted while the drug vial cap is under suction, thus prying the cap from its seal. The cap is still held by suction on the member until the suction is released at which time the cap falls into a trash bin.

The system 100 also preferably includes a fourth station (fluid transfer station) 170 for injecting or delivering a diluent into the medication contained in the sealed container and then subsequently mixing the medication and the diluent to form the medication composition (reconstituted medication) that is to be disposed into the prepared syringe. Alternatively, the station 170 can controllably deliver a predetermined dosage of pre-made medication. At this fluid transfer station 170, the prepared medication composition is withdrawn from the container (i.e., vial) and is then delivered into the syringe. For example, a cannula can be inserted into the sealed vial and the medication composition then aspirated into a cannula set. The cannula is then withdrawn from the vial and is then rotated relative to the rotary apparatus 130 so that it is in line with (above, below, etc.) the syringe. The unit dose of the medication composition is then delivered to the syringe, as well as additional diluent, if necessary or desired. This is referred to as a vial mode of operation where reconstitution of a drug is performed. The tip cap is then placed back on the syringe at a station 180. A station 190 prints and station 195 applies a label to the syringe and a device, such as a reader, can be used to verify that this label is placed in a correct location and the printing thereon is readable. Also, the reader can confirm that the label properly identifies the medication composition that is contained in the syringe and thus performs a safety check. The syringe is then unloaded from the rotary apparatus 130 at an unloading station 200 and delivered to a predetermined location, such as a new order bin, a conveyor, a sorting device, or a reject bin. The delivery of the syringe can be accomplished using a standard conveyor or other type of apparatus. If the syringe is provided as a part of the previously-mentioned syringe bandolier, the bandolier is cut prior at a station 198 located prior to the unloading station 200.

It will be appreciated that an initial labeling station 153 prior to the drug delivery station 170 (e.g., a station right after the load station 120) can be provided for applying a label with a unique identifier, such as a barcode, that uniquely identifies the syringe so that it can be tracked at any location as it is advanced from one station to another station. In other words, a reader 155 downstream of the initial labeling station 153 reads the unique identifier and associates the unique identifier with this particular syringe 10. This permits each drug order to be assigned one particular uniquely identified syringe which is logged into and tracked by the computer.

A robotic device is provided for moving objects relative to the transporter device (dial 130) and in particular, the robotic device can deliver and/or remove objects, such as the syringe 10 or the drug vials 60, relative to the dial 130. The robotic device thus typically has a gripper mechanism, such as a pair of grippers, for grasping and holding the object.

FIGS. 2-5 illustrate parts of the third station 150 for preparing a syringe 10, the fluid transfer station 170, and the station 180 for preparing the syringe for later use. As is known, a conventional syringe 10 includes a barrel 20 into which fluid is injected and contained and at a barrel tip, a cap 40 is provided to close off the barrel 20. A plunger 50 is slidingly received within the barrel 20 for both drawing fluid into the barrel and discharging fluid therefrom.

Figure 3:
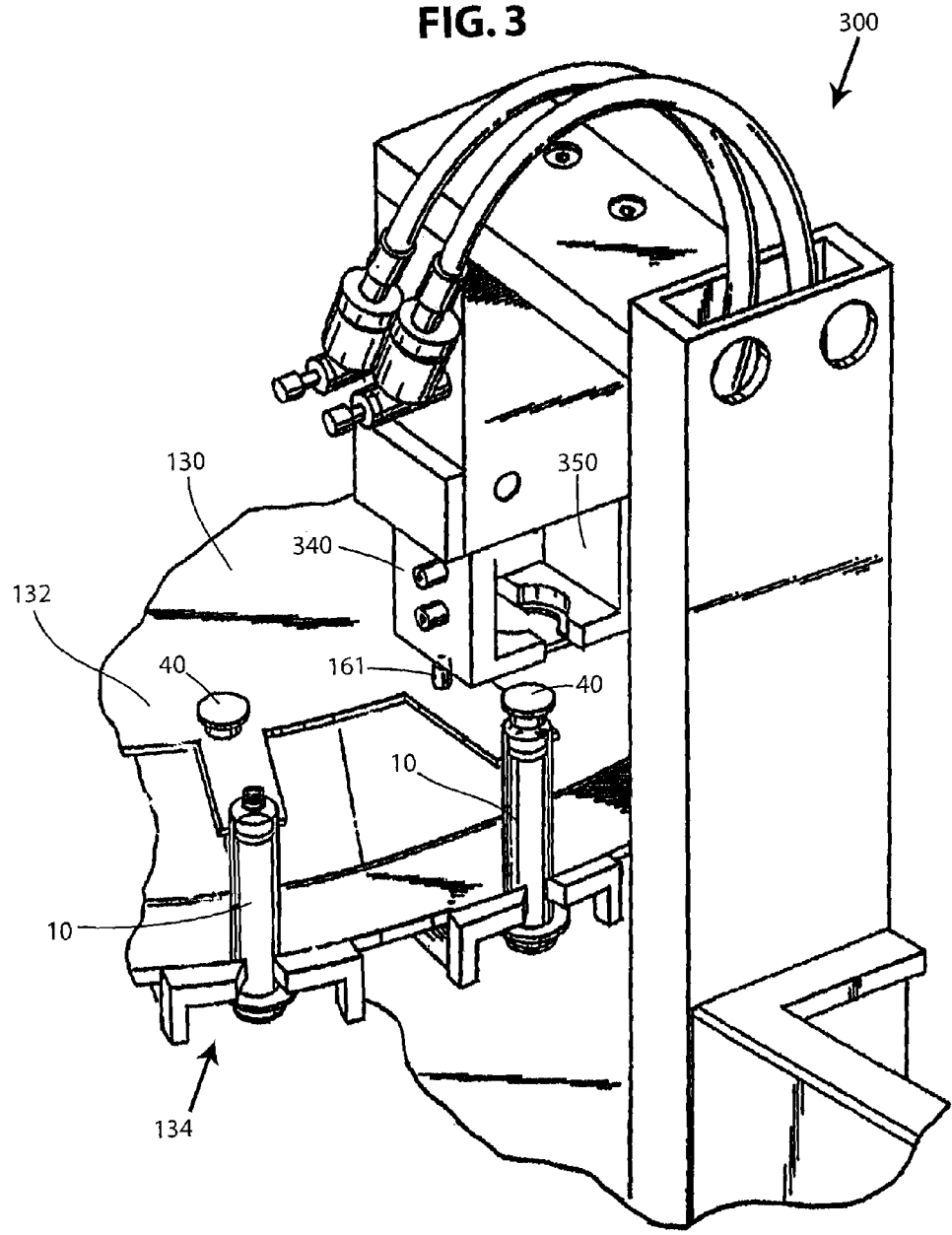
FIG. 3 is a local perspective view of an automated device for removing or replacing the safety tip cap from the syringe.

FIGS. 2-5 thus illustrate in more detail the stations and automated devices that are used in removal of the tip cap 40 from the barrel tip, the filling of barrel chamber with medication and the replacement of the tip cap 40 on the barrel tip. FIG. 3 is a perspective view of an automated device 300 at station 150 that removes the tip cap 40 from the barrel tip as the syringe 10 is prepared for receiving a prescribed dose of medication at station 170 of the automated medication preparation system 100. The device 300 is a controllable device that is operatively connected to a control unit, such as a computer, which drives the device 300 to specific locations at selected times. The control unit can be a personal computer that runs one or more programs to ensure coordinated operation of all of the components of the system 100. The device 300 and other suitable devices described in greater detail in U.S. Ser. No. 10/426,910, which is hereby incorporated by reference in its entirety.

In one aspect of the present invention, the cap 40 is removed by the device 300 at a first location and is then placed back on the syringe 10 at a second location that is different from the first location. The removed cap 40 advances with the syringe 10 since both are coupled to the transport device 130. In particular, the removed tip cap 40 is preferably placed back at a downstream of the location where the syringe 10 is filled with medication.

As previously mentioned, one exemplary rotary device 130 is a multiple station cam-indexing dial that is adapted to perform material handling operations. The dial 130 has an upper surface 132 and means 134 for securely holding one syringe 10 in a releasable manner and in a spaced relationship. Exemplary means 134 is disclosed in U.S. Pat. No. 6,915,823, which is incorporated herein by reference in its entirety.

A post 161 is provided for holding the tip cap 40 after its removal to permit the chamber to be filled with medication. The post 161 can also be formed on the upper surface 132 of the dial 130. Thus, the precise location of the post 161 can vary so long as the post 161 is located where the tip cap 40 can sit without interfering with the operation of any of the automated devices and also the post 161 should not be unnecessarily too far away from the held syringe 10 since it is desired for the automated devices to travel a minimum distance during their operation to improve the overall efficiency of the system 100. The specific shape of the post 161 can likewise vary so long as the post 161 can hold the tip cap 40 so that it remains on the post 161 during the rotation of the dial 130 as the associated syringe 10 is advanced from one station to another station.

While in one exemplary embodiment, the syringes 10 are fed to the rotary device 130 as part of a syringe bandolier (i.e., multiple syringes 10 are disposed in series and interconnected by a web), it will be appreciated that the syringes 10 can be fed to the rotary device 130 in any number of other ways. For example, the syringes 10 can be fed individually into and held individually on the rotary device 130 from a loose supply of syringes 10.

The automated device 300 is a robotic device and preferably, the automated device 300 is a linear actuator with a gripper. For example, the device 300 has first and second positionable gripping arms 340, 350 which are adjustable in at least one direction and which are coupled to and extend downwardly from the block member 330. For example, each of the gripping arms 340, 350 is movable at least in a direction along the y axis which provides the flexibility and motion control that is desirable in the present system 100. The gripping arms 340, 350 are programmed to work together in tandem so that both arms 340, 350 are driven to the same location and the same time. This permits an object, such as the cap 40, to be held and moved to a target holding location.

The precise movements of the gripper device 300 are described in the '910 application. In general, the gripper device 300 can be any robotic device that can hold and move an object, such as the tip cap 40, from one location to another location.

Figure 4:
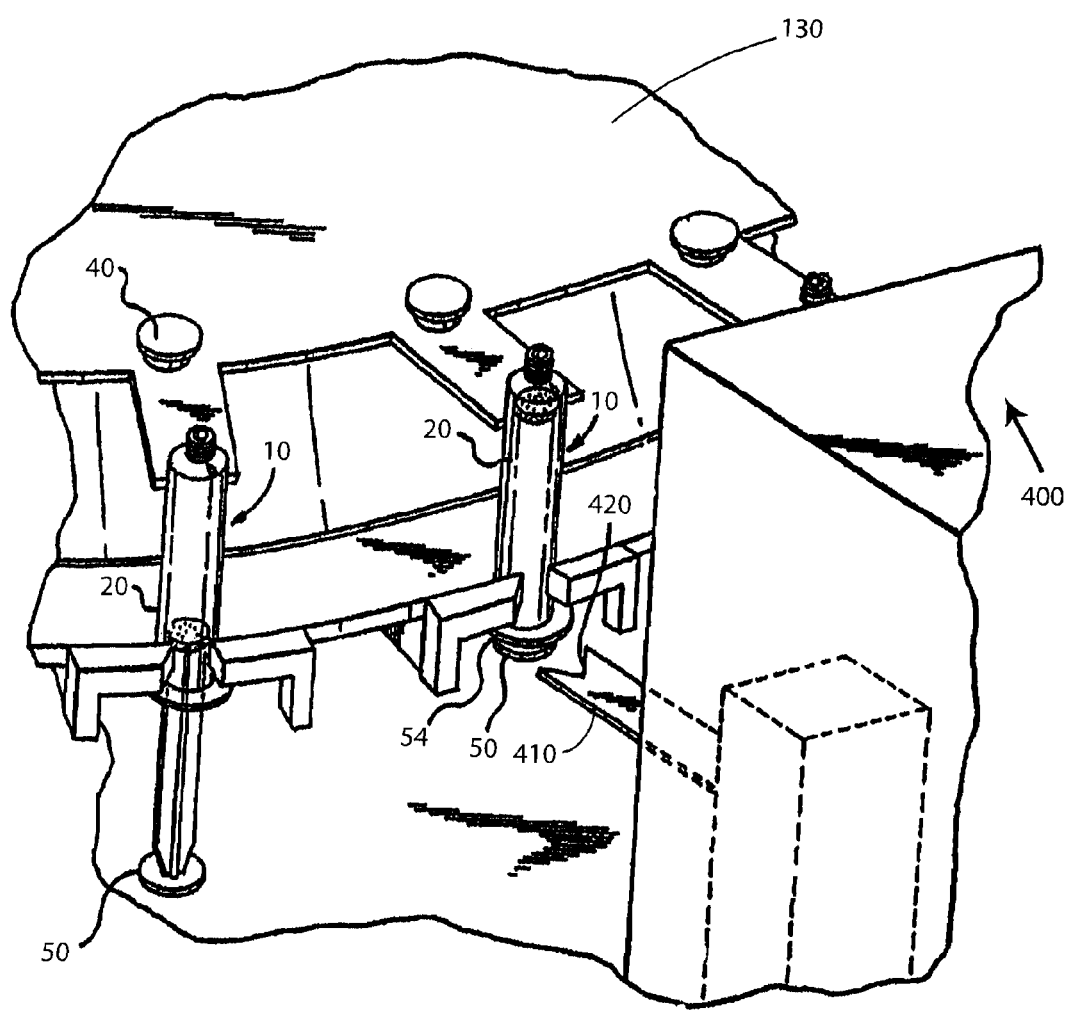
FIG. 4 is a local perspective view of a device for extending a plunger of the syringe.

Now referring to FIG. 4, the system 100 also includes a device 400 for extending the plunger 50 of one uncapped syringe 10 after it has had its tip cap 40 removed therefrom. For ease of illustration, the device 400, as well as the device 300, are described as being part of the third station 150 of the system 100. The device 400 extends the plunger 50 so that the syringe 10 can receive a desired dose based upon the particular syringe 10 being used and the type of application (e.g., patient's needs) that the syringe 10 is to be used for. The device 400 can have any number of configurations so long as it contains a feature that is designed to make contact with and withdraw the plunger 50. In one exemplary embodiment, the automated device 400 is a robotic device and preferably, the automated device 400 is a linear actuator with a gripper. For example, one exemplary device 400 is a mechanical device that has a movable gripper 410 that includes a gripping edge 420 that engages the flange 54 of the plunger 50, as shown in FIG. 4, and then the gripper 410 is moved in a downward direction causing the plunger 50 to be moved a predetermined amount. For example, the gripper 410 can be the part of an extendable/retractable arm that includes the gripping edge 420 for engaging the syringe 10 above the plunger flange 54. When an actuator or the like (e.g., stepper motor) causes the gripper 410 to move in a downward direction, the gripping edge 420 seats against the flange 54 and further movement of the gripper 410 causes the extension of the plunger 50. Once the plunger 50 has been extended the prescribed precise distance, the gripper 410 moves laterally away from the plunger 50 so that the interference between the flange 54 of the plunger 50 and the gripping edge 420 no longer exits. In other words, the gripper 410 is free of engagement with the plunger 50 and can therefore be positioned back into its initial position by being moved laterally and/or in an up/down direction (e.g., the gripper 410 can move upward to its initial position). An exemplary plunger extending device is described in commonly assigned U.S. patent application Ser. No. 10/457,066, which is hereby incorporated by reference in its entirety.

Thus, the device 400 complements the device 300 in getting the syringe 10 ready for the fluid transfer station at which time, a prescribed amount of medication or other medication is dispensed into the chamber 30 of the barrel 20 as will be described in greater detail hereinafter.

Of course, it will be appreciated that the syringes 10 can be provided without caps 40 and thus, the device 300 is not needed to remove caps 40 if the syringes 10 are loaded onto dial 130 without caps 40.

The device 400 is part of the overall programmable system and therefore, the distance that the gripper 410 moves corresponds to a prescribed movement of the plunger 50 and a corresponding increase in the available volume of the chamber of the barrel 20. For example, if the prescribed unit dose for a particular syringe 10 is 8 ml, then the controller instructs the device 400 to move the gripper 410 a predetermined distance that corresponds with the plunger 50 moving the necessary distance so that the volume of the barrel chamber is at least 8 ml. This permits the unit dose of 8 ml to be delivered into the barrel chamber. As described below, the device 400 can be operated multiple times with reference to one syringe 10 in that the plunger 50 can be extended a first distance during a first operation of the device 400 and a second distance during a subsequent second operation of the device 400.

In one example, after the syringe 10 has been prepared by removing the tip cap 40 and extending the plunger 50 a prescribed distance, the syringe 10 is then delivered to the fluid transfer station 170 where a fluid transfer device 500 prepare and delivers the desired amount of medication.

Figure 5:
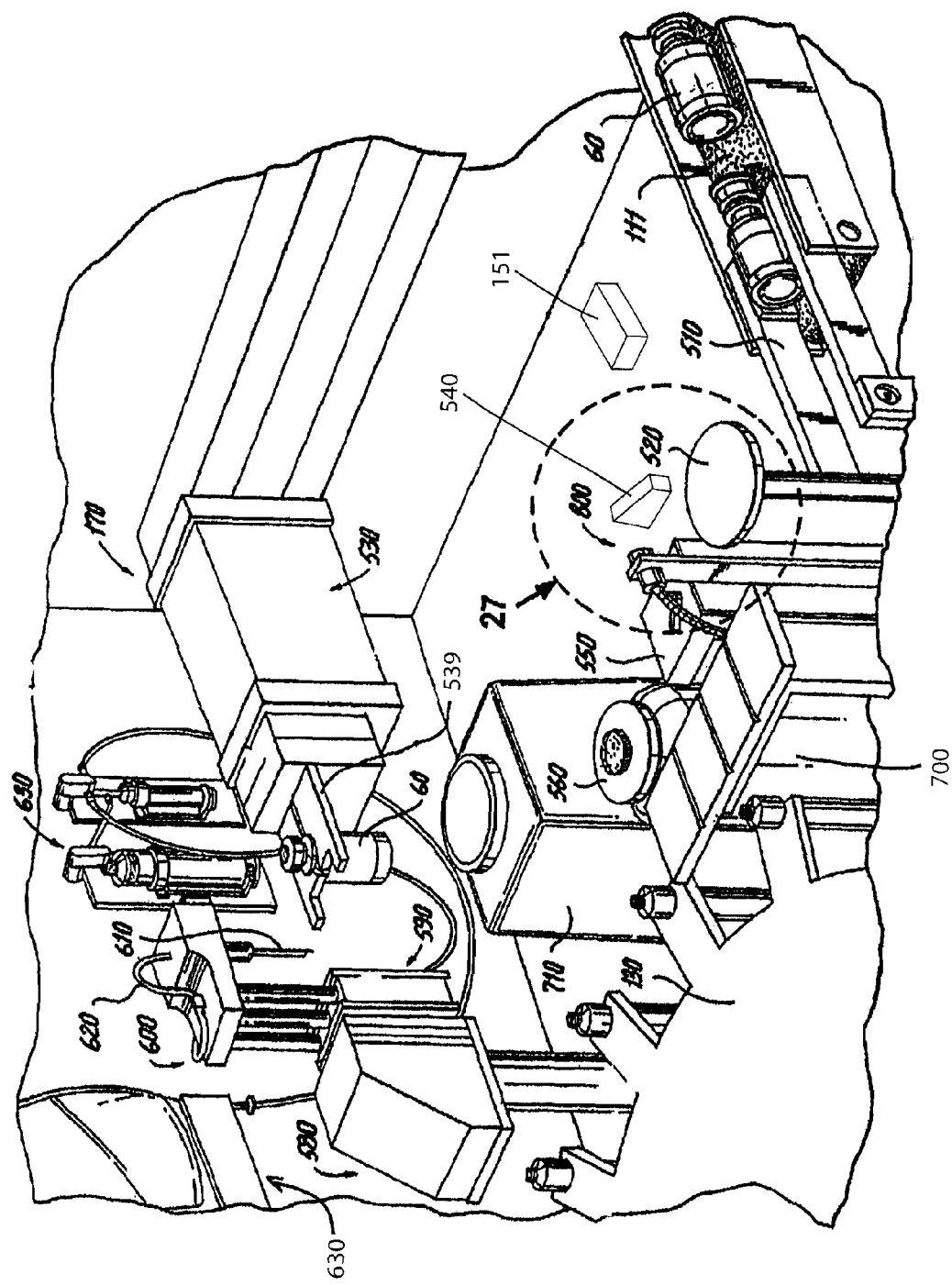
FIG. 5 is a local perspective view of fluid transfer and vial preparation equipment in a fluid transfer area of the automated system.

Now turning to FIG. 5 in which a drug preparation area is illustrated in greater detail to show the individual components thereof. More specifically, a drug transfer area for the vial mode of operation of the system 100 is illustrated and is located proximate the rotary dial 130 so that after one drug vial 60 is prepared (reconstituted), the contents thereof can be easily delivered to one or more syringes 10 that are securely held in nested fashion on the rotary dial 130. As previously mentioned, drug vials 60 are stored typically in the storage cabinet 110 and can be in either liquid form or solid form or even be empty. A driven member, such as a conveyor belt 111, delivers the drug vial 60 from the cabinet 110 to a first robotic device (e.g., a pivotable vial gripper mechanism) 510 that receives the vial 60 in a horizontal position and after gripping the vial with arms (grippers) or the like, the mechanism 510 is operated so that the vial 60 is moved to a vertical position relative to the ground and is held in an upright manner.

The mechanism 510 is designed to deliver the vial 60 to a rotatable pedestal 520 that receives the vial 60 once the grippers of the mechanism 510 are released. The vial 60 sits upright on the pedestal 520 near one edge thereof that faces the mechanism 510 and is then rotated so that the vial 60 is moved toward the other side of the pedestal 520. It will be understood that any number of different robotic mechanisms can be used to handle, move and hold the vial.

As the pedestal rotates, the vial 60 is scanned as by a barcode reader 151 or the like and preferably a photoimage thereof is taken and the vial 60 is identified. If the vial 60 is not the correct vial, then the vial 60 is not used and is discarded using a gripper device that can capture and remove the vial 60 from the pedestal before it is delivered to the next processing station. The central control has a database that stores all the identifying information for the vials 60 and therefore, when a dose is being prepared, the controller knows which vial (by its identifying information) is to be delivered from the cabinet 110 to the pedestal 520. If the scanning process and other safety features does not result in a clear positive identification of the vial as compared to the stored identifying information, then the vial is automatically discarded (e.g., returned to a further inspection station) and the controller will instruct the system to start over and retrieve a new vial.

The reader, such as a scanner, 151 can also read the vial 60 to ensure that the proper vial 60 has been delivered and gripped by the robotic device. This is another safety check and can be implemented with barcodes or the like. The reader 151 initially reads the barcode or other identifying information contained on the vial 60 and this read information is compared to a stored database that contains the inputted drug information. If the product identification information does not match, the operator is notified and the vial 60 is not advanced to the next station.

If the vial 60 is identified as being the correct vial, then a vial gripper device (robotic device) 530 moves over to the pedestal for retrieving the vial 60 (alternatively, this robotic device can be the same robotic device that delivers the vial 60 to the pedestal). The vial gripper device 530 is configured to securely grip and carry the vial in a nested manner to the next stations as the drug is prepared for use. Details and operation of the vial gripper device 530 are described in detail in U.S. patent application Ser. No. 11/434,850, which is hereby incorporated by reference in its entirety. The robotic device 530 includes a pair of grippers or arms 539 (gripper unit) that are positionable between closed and open positions with the vial 60 being captured between the arms in the closed position in such a manner that the vial 60 can be securely moved and even inverted and shaken without concern that the vial 60 will become dislodged and fall from the arms. The arms thus have a complementary shape as the vial 60 so that when the arms close, they engage the vial and nest around a portion (e.g., neck portion) of the vial 60 resulting in the vial 60 being securely captured between the arms. As with some of the other components, the arms can be pneumatically operated arms or some other mechanical devices.

In order to retrieve the vial 60 from the pedestal 520, the device 530 is driven forward and then to one side so that it is position proximate the pedestal 520. The gripper unit 539 is then moved downward so that the arms, in their open position, are spaced apart with the vial 60 being located between the open arms. The gripper unit 539 is then actuated so that the arms close and capture the vial 60 between the arms. Next the robotic device 530 is moved upward and the device 530 is driven back to the opposite side so as to introduce the vial 60 to the next station. The vial 60 is also inverted by inversion of the gripper unit 539 so that the vial 60 is disposed upside down.

Figure 7:
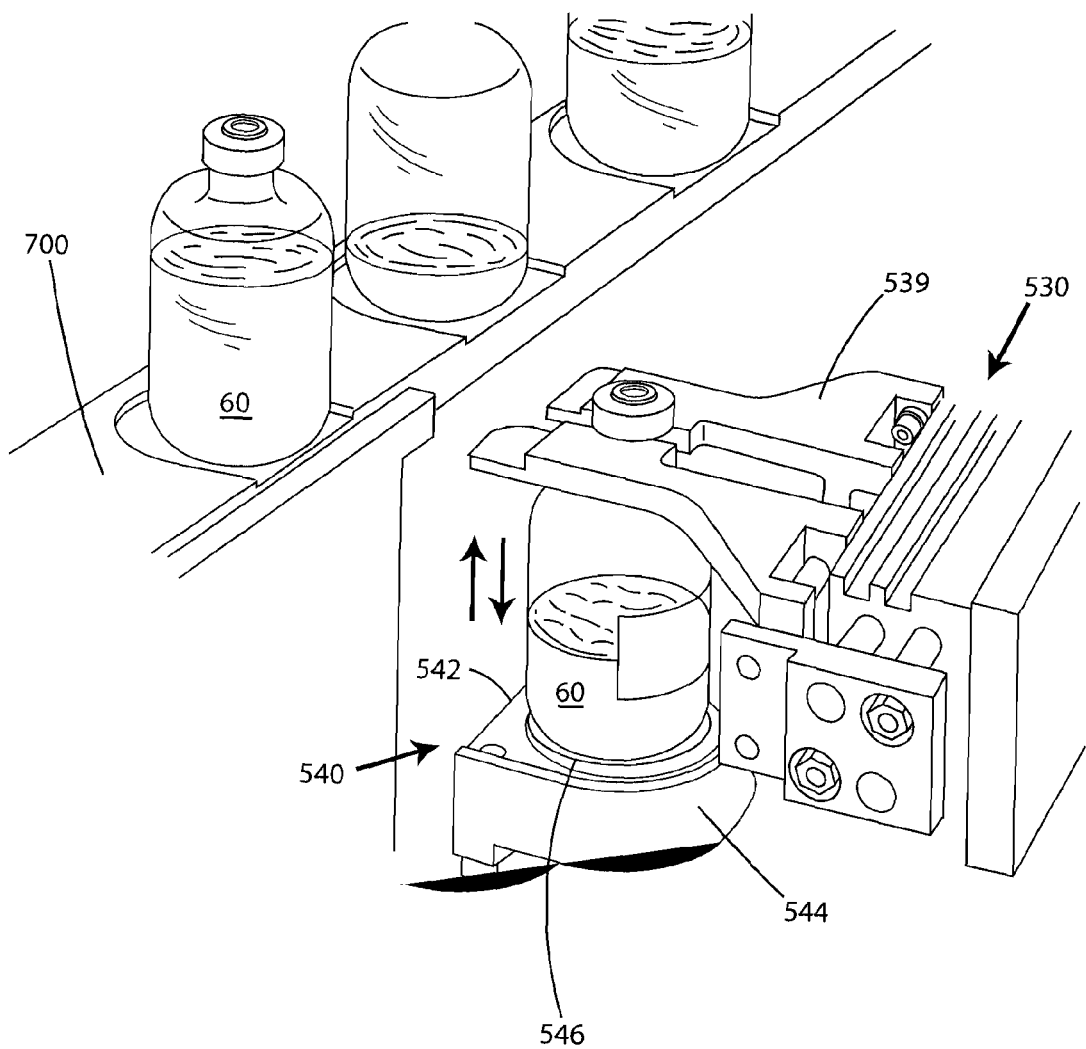
FIG. 7 is a local perspective view of a multi-use vial holding station and a vial weigh station.

The vial 60 can then be delivered to a weigh station 540 (FIG. 7) where the weight of the vial with solid medication (or an empty vial or any other object) is measured and stored in the computer system. Any number of different devices, such as scales, can be used to weigh the vial; however, one exemplary device for weighing the vial 60 and any other object for that matter, is a load cell 542. Load cell 542 is a transducer for the measurement of force or weight, usually based on a strain gauge bridge or vibrating wire sensor. In particular and as shown in FIG. 7, the load cell 542 includes a housing or body 544 that contains the working components and electronics of the load cell 542 and a platform 546 on which the item, in this case, the vial, to be weighed is placed.

The load cell 542 is part of an overall automated and integrated system and therefore, it contains software that communicates with the master controller so that the operation of the complete system 100 can be controlled, including the movement of the robotic device 530 that holds and transport the vial 60 from one location to another location. As shown in FIG. 7, the vial 60 is held by the robotic device about the neck portion and can therefore be delivered onto the load cell platform 546. In one embodiment, the robotic device moves the vial 60 from the pedestal 520 to the platform 546.

The software controlling the robotic device is configured so that the vial grippers of the robotic device are first approximately level with the standby pedestal 520 and at this point, the software of the load cell gather a predetermined number, such as 10-15 (e.g., 15) weights from the load cell 542 which are considered the tare weight. The vial 60 is then shuttled down to a predetermined distance, such as 2.5 mm, above the load cell platform 546. From this predetermined distance (e.g., 2.5 mm), the load cell software shuttles the vial 60 down towards the load cell platform 546 very slowly, while monitoring the weights returned by the load cell 542 to determine the exact moment the vial makes contact with the platform 546 (i.e., which will register a marked increase in observed weight). At the moment the vial contact the platform, the software instructs the vial grippers to open and all vertical movement of the vial is stopped. A predetermined time, such as 0.5 seconds, after the vial grippers open, the software collects a predetermined number, such as 10-15 (e.g., 15) weight measurements from the load cell, which shall be considered the weight of the vial and the load cell platform.

Figure 11:
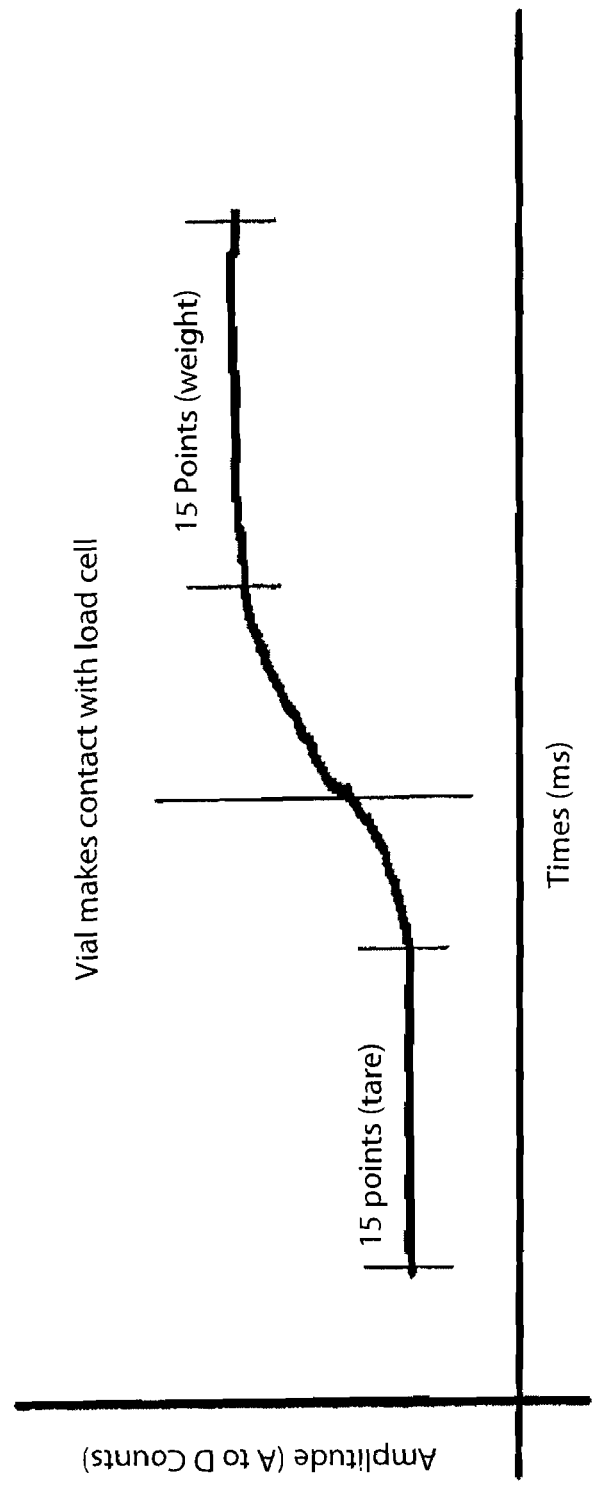
FIG. 11 is a graph of the data obtained by a load cell for determining a weight of the contents of the vial to ensure proper reconstitution of the medication.

The data collected by the load cell can be processed in any number of different ways and in one embodiment, as shown in FIG. 11, a graph is created where the x axis is the measured amplitude (A to D counts) and the y axis is the time (ms). The point at which the vial makes contact with the load cell 542 is indicated at line 545. The vial weight (A to D counts) is equal to the measured weight-tare. The vial weight (grams) is equal to (vial weight (A to D counts)*slope)+intercept.

As will be described below, since the initial weight of the vial is measured and stored and later, the weight of the reconstituted drug in the vial is calculated, a safety check can be performed to determine if the proper drug product was fabricated.

Prior to the vial 60 being delivered to the weigh station 540, the inverted vial 60 is delivered to a station 550 where the vial 60 is prepared by removing the safety cap from vial 60. This station 550 can therefore be called a vial decapper station. Any number of devices can be used at station 550 to remove the safety cap from the vial. For example, several exemplary decapper devices are disclosed in commonly-assigned U.S. Pat. No. 6,604,903 which is hereby incorporated by reference in its entirety. After the vial 60 is decapped, the vial is then delivered, still in the inverted position, to a cleaning station 560 where the exposed end of the vial is cleaned. For example, underneath the removed vial safety cap, there is a septum that can be pierced to gain access to the contents of the vial. The cleaning station 560 can be in the form of a swab station that has a wick saturated with a cleaning solution, such as an alcohol. The exposed area of the vial 60 is cleaned by making several passes over the saturated wick which contacts and baths the exposed area with cleaning solution. After the vial 60 is cleaned at the station 560, the gripper unit 539 rotates so that the vial 60 is returned to its upright position and remains held between the gripper arms.

The device 530 then advances forward to the fluid transfer station 170 according to one embodiment. The fluid transfer station 170 is an automated station where the medication (drug) can be processed so that it is in a proper form for delivery (injection) into one of the syringes 10 that is coupled to the rotary dial 130. As mentioned before, the fluid transfer station 170 is used during operation of the system, at least partially, in a vial mode of operation. When the vial 60 contains only a solid medication and it is necessary for a diluent (e.g., water or other fluid) to be added to liquify the solid, this process is called a reconstitution process. Alternatively and as will be described in detail below, the medication can already be prepared and therefore, in this embodiment, the fluid transfer station is a station where a precise amount of medication is simply aspirated or withdrawn from the vial 60 and delivered to the syringe 10.

For purpose of illustration, the reconstitution process is first described. After having been cleaned, the vial 60 containing a prescribed amount of solid medication is delivered in the upright position to the fluid transfer station 170 by the device 530. As will be appreciated, the device 530 has a wide range of movements in the x, y and z directions and therefore, the vial 60 can easily be moved to a set fluid transfer position. At this position, the vial 60 remains upright and a fluid transfer device 580 is brought into position relative to the vial 60 so that an automated fluid transfer can result therebetween. More specifically, the fluid transfer device 580 is the main means for both discharging a precise amount of diluent into the vial 60 to reconstitute the medication and also for aspirating or withdrawing the reconstituted medication from the vial 60 in a precise, prescribed amount. The device 580 is a controllable device that is operatively connected to a control unit, such as a computer, which drives the device 580 to specific locations at selected times and controls with a high degree of precision the operation and discharge of medication. The control unit can be a personal computer that runs one or more programs to ensure the coordinated operation of all of the components of the system 100.

Figure 6:
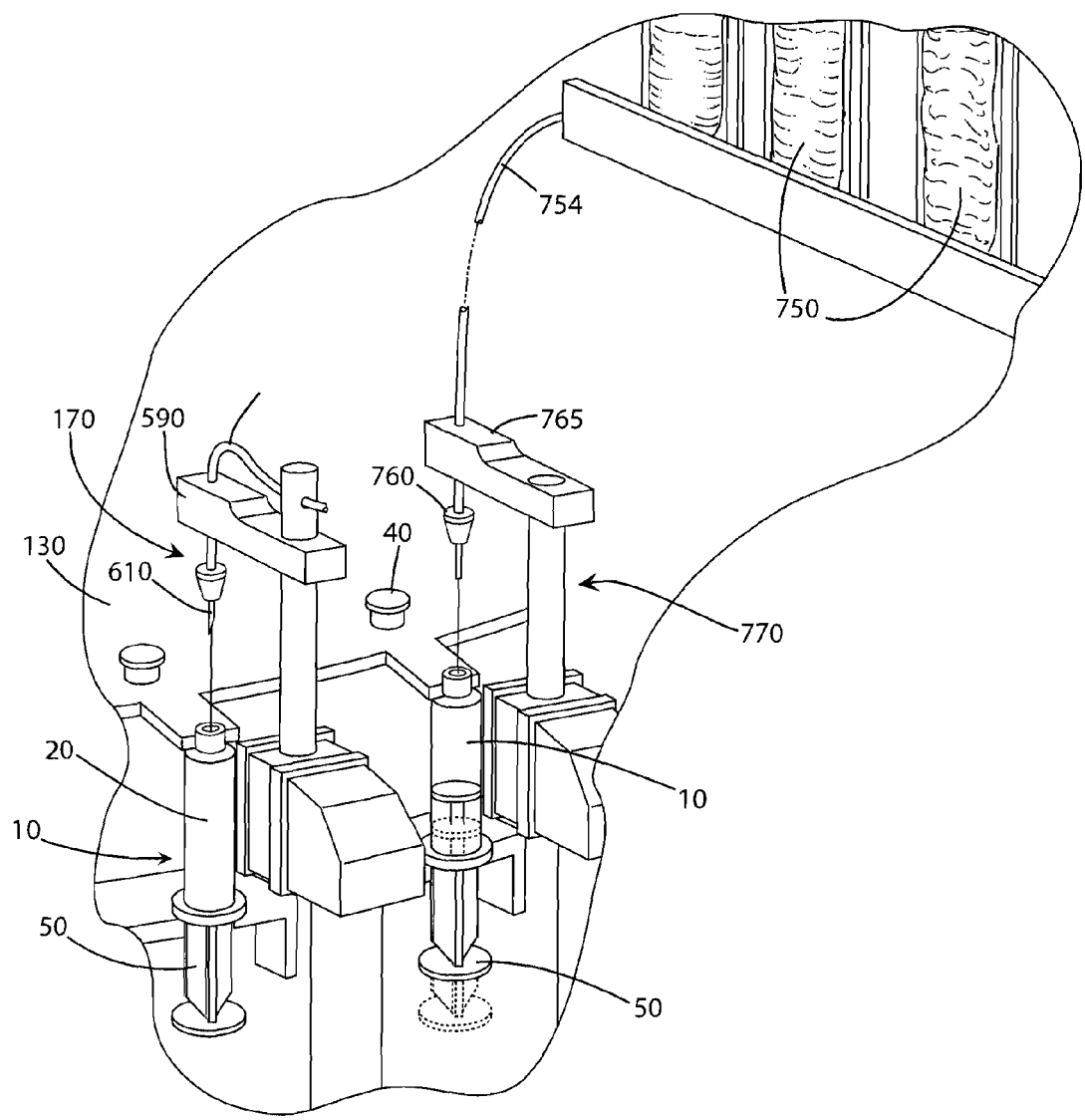
FIG. 6 is a local perspective view of first and second fluid delivery devices that form a part of the system of FIG. 2.

As illustrated in FIGS. 1 and 6, one exemplary fluid transfer device 580 is a robotic device having a movable cannula unit 590 that can be moved in a controlled up and down and side-side, etc., manner so to either lower it or raise it relative to the vial 60 in the fluid transfer position and to move it into the proper position. For example, the cannula unit 590 can be pneumatically operated or operated by an electric motor or some other means to cause the controlled movement of the cannula unit 590.

At one end of the cannula unit 590, a cannula 610 is provided. The cannula 610 has one end that serves to pierce the septum of the vial 60 and an opposite end that is connected to a main conduit 620 that serves to both deliver diluent to the cannula 610 and ultimately to the vial 60 and receive aspirated reconstituted medication from the vial 60. Preferably, the cannula 610 is of the type that is known as a vented cannula which can be vented to atmosphere as a means for eliminating any dripping or spattering of the medication during an aspiration process. More specifically, the use of a vented needle to add (and withdraw) the fluid to the vial overcomes a number of shortcoming associated with cannula fluid transfer and in particular, the use of this type of needle prevents backpressure in the vial (which can result in blow out or spitting or spraying of the fluid through the piercing hole of the cannula). The venting takes place via an atmospheric vent that is located in a clean air space and is formed in a specially designed hub that is disposed over the needle. By varying the depth that the needle penetrates the vial, the user can control whether the vent is activated or not. It will be appreciated that the venting action is a form of drip control (spitting) that may otherwise take place.

Moreover, the cannula 610 is also preferably of the type that is motorized so that the tip of the cannula 610 can move around within the vial 60 so that cannula 610 can locate and aspirate every last drop of the medication. In other words, the cannula 610 itself is mounted within the cannula unit 590 so that it can move slightly therein such that the tip moves within the vial and can be brought into contact with the medication wherever the medication may lie within the vial 60. Thus, the cannula 610 is driven so that it can be moved at least laterally within the vial 60.

An opposite end of the main conduit 620 is connected to a fluid pump system 630 that provides the means for creating a negative pressure in the main conduit 620 to cause a precise amount of fluid to be withdrawn into the cannula 610 and the main conduit 620, as well as creating a positive pressure in the main conduit 620 to discharge the fluid (either diluent or medication) that is stored in the main conduit 620 proximate the cannula 610. One exemplary fluid pump system 630, as well as the operation thereof, is described in great detail in the '823 patent, which has been incorporated by reference. The net result is that the prescribed amount of diluent that is needed to properly reconstitute the medication is delivered through the cannula 610 and into the vial 60. Accordingly, the cannula 610 pierces the septum of the vial and then delivers the diluent to the vial and the vial 60 can be inverted to cause agitation and mixing of the contents of the vial or the vial can be delivered to a separate mixing device to cause the desired mixing of the contents.

After the medication in the vial 60 has been reconstituted as by inversion of the vial and/or mixing, as described herein, the fluid pump system 630 is then operated so that a prescribed amount of medication is aspirated or otherwise drawn from the vial 60 through the cannula 610 and into the main conduit 620. Before the fluid is aspirated into the main conduit 620, an air bubble is introduced into the main conduit 620 to serve as a buffer between the diluent contained in the conduit 620 to be discharged into one vial and the aspirated medication that is to be delivered and discharged into one syringe 10. It will be appreciated that the two fluids (diluent and prepared medication) can not be allowed to mix together in the conduit 620. The air bubble serves as an air cap in the tubing of the cannula and serves as an air block used between the fluid in the line (diluent) and the pulled medication. According to one exemplary embodiment, the air block is a ⅒ ml air block; however, this volume is merely exemplary and the size of the air block can be varied.

After aspirating the medication into the main conduit 620, the fluid transfer device 580 is rotated as is described below to position the cannula 610 relative to one syringe 10 that is nested within the rotary dial 130. The pump mechanism 630 is actuated to cause the controlled discharge of the prescribed amount (dosage) of medication through the cannula 610. As the pump mechanism 630 is operated, the air block continuously moves within the main conduit 620 toward the cannula 610. When all of the pulled (aspirated) medication is discharged, the air block is positioned at the end of the main conduit signifying that the complete pulled medication dose has been discharged; however, none of the diluent that is stored within the main conduit 620 is discharged into the syringe 10 since the fluid transfer device 580, and more particularly, drivers or the like of the system, operate with such precision that only the prescribed medication that has been previously pulled into the main conduit 620 is discharged into the vial 60.

It will be appreciated that the fluid transfer device 580 may need to make several aspirations and discharges of the medication into the vial 60 in order to inject the complete prescribed medication dosage into the vial 60. In other words, the cannula unit 590 can operate to first aspirate a prescribed amount of fluid into the main conduit 620 and then is operated so that it rotates over to and above one syringe 10 on the rotary dial 130, where one incremental dose amount is discharged into the vial 60. After the first incremental dose amount is completely discharged into the syringe 10, the cannula unit 590 is brought back the fluid transfer position where the fluid transfer device is operated so that a second incremental dose amount is aspirated into the main conduit 620 in the manner described in detail hereinbefore. The cannula unit 590 is brought back to the rotary dial 130 above the syringe 10 that contains the first incremental dose amount of medication. The cannula 610 is then lowered so that the cannula tip is placed within the interior of the syringe 10 and the cannula unit 590 is operated so that the second incremental dose amount is discharged into the syringe 10. The process is repeated until the complete medication dose is transferred into the syringe 10.

In another aspect of the present invention is that in the vial mode, the cannula unit 590 can be configured so that it withdraws a predetermined amount of medication that is to be delivered successively to multiple syringes. In other words, a multidose draw can be performed by the cannula unit 590 which then delivers a prescribed amount of medication to each syringe 10 from the initial multidose draw. For example, if there is a medication order for 5 different syringes each to be filled with 1 ml of medication, then the cannula unit 590 is operated to withdraw (aspirate) 5 ml of medication at once and then in a controlled manner deliver 1 ml of medication into each syringe 10 in a successive manner. In this manner, one medication draw operation can be performed which provides the source of medication for a plurality of medication fills within different syringes.

It will further be appreciated that the cannula unit 590 can be configured so that it can be operated at varying speeds of aspiration. For example, the software associated with the cannula unit 590 can offer the operator a number of different aspiration programs to choose from or the operator can program the unit 590 with a unique aspiration process or program by entering or inputting aspiration instructions. For example, the unit 590 can operate by first aspirating the medication at a first speed and for a first time period and then aspirating the medication at a second speed for a second time period. According to one embodiment, the first speed is greater than the second speed and the first time period is greater than the second time period; however, the opposite can be equally true and it will further be appreciated that there may be more than 2 distinct aspiration phases. For example, there can be a first aspiration phase that operates at a first aspiration speed, a second aspiration phase that operates at a second speed and a third aspiration phase that operates at a third aspiration speed. The speed of the aspiration can be varied by simply varying the speed of the pump. In this manner, the initial aspiration of the medication can operate at a higher speed and then when only a small amount of medication remains, the aspiration speed can be reduced so as to controllably withdraw the last portion of the medication that is contained in the container.

In addition, the reconstitution equipment, including the cannula unit 590, can possess various motions, including a gentle inversion to "wet" the solid drug in the vial 60 with the diluent that was added to the vial 60 and an agitation motion which causes the drug to go into solution. The system 100, and in particular, the reconstitution module thereof, is configured to operate in this manner since the reconstitution process uses both motions based upon key drug characteristics. A database controls the differences observed from drug to drug. In one embodiment, the robotic gripper holds the drug vial 60 during the agitation cycle so that is does not become dislodged. The associated software preferably possesses a QA function that enables the drug to be tested under various conditions to assure that the settings effect putting the drug into solution, and the ability to have the reconstituted drug manually observed, by the robotic gripper removing the drug from the reconstitution station 170 and presenting the vial 60 to a window (when the system 100 is contained within an enclosed structure as described below) for an operator to look at the vial 60 and enter their observations into a reconstitution QA database. If the drug was not fully in solution, the entry into the QA database can be used to adjust the formulary to require an additional increment of agitation time.

In other words, the software is designed so that once the operator enters the drug order, the master controller accesses the reconstitution database that includes detailed instructions as to how to prepare the reconstituted drug of the order and part of these instructions include instructions on the aspiration process as discussed below. In particular, once the drug type of the order is identified, the aspiration instructions are determined, including the number, length and characteristics of the agitation phases and motions, and then the controller instructs the equipment to execute these instructions.

In yet another embodiment, a prescribed dosage of medication can be drawn from the vial 60 by mating a syringe 10 with the vial 60 as by inserting the needle (vented cannula) of the syringe into and through the septum of the vial 60 and then extending the plunger a predetermined, precise distance so as to draw a precise amount dosage into the syringe from the drug vial 60. The device and method for controlling the extension of the plunger is described in great detail herein.

Once the syringe 10 receives the complete prescribed medication dose, the vial 60 that is positioned at the fluid transfer position can either be (1) discarded or (2) it can be delivered to a holding station 700 where it is cataloged and held for additional future use. More specifically, the holding station 700 serves as a parking location where a vial that is not completely used can be used later in the preparation of a downstream syringe 10. In other words, the vials 60 that are stored at the holding station 700 are labeled as multi-use medications that can be reused. These multi-use vials 60 are fully reconstituted so that at the time of the next use, the medication is only aspirated from the vials 60 as opposed to having to first inject diluent to reconstitute the medication. The user can easily input into the database of the master controller which medications are multi-use medications and thus when the vial 60 is scanned and identified prior to being delivered to the fluid transfer position, the vial 60 is identified and marked as a multi-use medication and thus, once the entire medication dose transfer has been performed, the vial gripper device 530 is instructed to deliver the vial 60 to the holding station 700. Typically, multi-use medications are those medications that are more expensive than other medications and also are those medications that are used in larger volumes (quantities) or are stored in larger containers and therefore come in large volumes.

The holding station 700 is simply a location where the multi-use vials can be easily stored. For example, the holding station 700 is preferably a shelf or even a cabinet that contains a flat surface for placing the vials 60. Preferably, there is a means for categorizing and inventorying the vials 60 that are placed at the holding station 700. For example, a grid with distinct coordinates can be created to make it easy to determine where each vial 60 is stored within the holding station 700.

Once the device 530 has positioned the vial 60 at the proper location of the holding station 700, the gripper unit is operated so that the arms thereof release the vial 60 at the proper location. The device 530 then returns back to its default position where it can then next be instructed to retrieve a new vial 60 from the pedestal 520.

If the vial 60 is not a multi-use medication, then the vial 60 at the fluid transfer position is discarded. When this occurs, the device 530 moves such that the vial 60 is positioned over a waste chute or receptacle and then the gripper unit is actuated to cause the vial 60 to drop therefrom into the waste chute or receptacle. The device 530 is then ready to go and retrieve a new vial 60 that is positioned at the pedestal 520 for purposes of either reconstituting the medication or simply aspirating an amount of medication therefrom or a vial from the holding station 700 can be retrieved.

As previously mentioned, during the reconstitution process, it is often necessary or preferable to mix the medication beyond the mere inversion of the vial and therefore, the vial 60 can be further agitated using a mixing device or the like 710. In one embodiment, the mixing device 710 is a vortex type mixer that has a top surface on which the vial 60 is placed and then upon actuation of the mixer, the vial 60 is vibrated or otherwise shaken to cause all of the solid medication to go into solution or cause the medication to be otherwise mixed. In yet another embodiment, the mixing device is a mechanical shaker device, such as those that are used to hold and shake paint cans. For example, the vial 60 can be placed on support surface of the shaker and then an adjustable hold down bar is manipulated so that it travels towards the vial and engages the vial at an end opposite the support surface. Once the vial 60 is securely captured between these two members, the shaker device is actuated resulting in the vial 60 being shaken to agitate the medication and ensure that all of the medication properly goes into solution. In addition, the mixing device 710 can also be configured so that it is in the form of a robotic arm that holds the vial by means of gripper members (fingers) and is operatively connected to a motor or the like which serves to rapidly move the arm in a back and forth manner to cause mixing of the medication.

As briefly mentioned before, the entire system 100 is integrated and automated and also utilizes a database for storing identifying data, mixing instructions, and other information to assist in the preparation of the medication. There are also a number of safety features and check locations to make sure that the medication preparation is proceeding as it should.

For example, the database includes identifying information so that each vial 60 and syringe 10 can be carefully kept track of during each step of the process. For example, the reader (e.g., barcode scanner) 151 and the photoimaging equipment serve to positively identify the vial 60 that is delivered from the drug storage 110. Typically, the user will enter one or more medication preparation orders where the system 100 is instructed to prepare one or more syringes that contain specific medication. Based on this entered information or on a stored medication preparation order that is retrieved from a database, the vial master controller determines at which location in the cabinet the correct vial 60 is located. That vial 60 is then removed using a robotic gripper device (not shown) and is then placed on the conveyor belt 111 and delivered to the mechanism 510 pivots upright so that the vial 60 is moved a vertical position relative to the ground and is held in an upright manner and is then delivered to the rotatable pedestal 520. At the pedestal 520, the vial 60 is scanned to attempt to positively identify the vial 60 and if the scanned identifying information matches the stored information, the vial 60 is permitted to proceed to the next station. Otherwise, the vial 60 is discarded.

Once the vial 60 is confirmed to be the right vial it proceeds to the fluid transfer position. The master controller serves to precisely calculate how the fluid transfer operation is to be performed and then monitors the fluid transfer operations has it is occurring. More specifically, the master controller first determines the steps necessary to undertake in order to perform the reconstitution operation. Most often during a reconstitution operation, the vial 60 that is retrieved from the drug storage 110 contains a certain amount of medication in the solid form. In order to properly reconstitute the medication, it is necessary to know what the desired concentration of the resulting medication is to be since this determines how much diluent is to be added to the vial 60. Thus, one piece of information that the user is initially asked to enter is the concentration of the medication that is to be delivered to the patient as well as the amount that is to be delivered. Based on the desired concentration of the medication, the master controller is able to calculate how much diluent is to be added to the solid medication in the vial 60 to fully reconstitute the medication. Moreover, the database also preferably includes instructions as to the mixing process in that the mixing device is linked to and is in communication with the master controller so that the time that the mixing device is operated is stored in the database such that once the user inputs the medication that is to be prepared and once the vial 60 is scanned and identified, the system (master controller or CPU thereof) determines the correct of time that the vial 60 is to be shaken to ensure that all of the medication goes into solution.

Once the master controller determines and instructs the working components on how the reconstitution operation should proceed, the master controller also calculates and prepares instructions on how many distinct fluid transfers are necessary to deliver the prescribed amount of medication from the vial 60 to the syringe 10. In other words, the cannula unit 590 may not be able to fully aspirate the total amount of medication from the vial 60 in one operation and therefore, the master controller determines how many transfer are needed and also the appropriate volume of each aspiration so that the sum of the aspiration amounts is equal to the amount of medication that is to be delivered to the syringe 10. Thus, when multiple aspiration/discharge steps are required, the master controller instructs and controls the operation of the pump mechanism so that the precise amounts of medication are aspirated and then discharged into the syringe 10. As previously described, the pump mechanism operates to cause the proper dose amount of the medication to be first aspirated from the vial and then discharged into the syringe. This process is repeated as necessary until the correct dose amount is present in the syringe 10 in accordance with the initial inputted instructions of the user.

After transferring the proper precise amount of medication to one syringe 10, the master controller instructs the rotary dial to move forward in an indexed manner so that the next empty syringe 10 is brought into the fluid transfer position. The cannula 610 is also preferably cleaned after each medication dose transfer is completed so as to permit the cannula 610 to be reused. There are a number of different techniques that can be used to clean the cannula 610 between each medication transfer operation. For example, the cleaning equipment and techniques described in commonly assigned U.S. Pat. No. 6,616,771 and U.S. patent application Ser. No. 10/457,898 (both of which are hereby incorporated by reference in their entireties) are both suitable for use in the cleaning of the cannula 610.

In one embodiment, the cannula 610 is rotated and positioned so that the needle of the cannula 610 is lowered into a bath so that fluid is expelled between the inside hubs of the syringe 10 for cleaning of the interior components of the cannula 610. The cannula 610 is then preferably dipped into a bath or reservoir to clean the outside of the cannula 610. In this manner, the cannula 610 can be fully cleaned and ready for a next use without the need for replacement of the cannula 610, which can be quite a costly endeavor.

In yet another embodiment, a medication source, such as a bag that is filled with liquid medication that has already been properly reconstituted, is connected to an input portion of a peristaltic pump by means of a first conduit section. A second conduit section is connected to an output port of the pump and terminates in a connector. The connector is of the type that is configured to hermetically seal with an open barrel tip of the syringe 10 that is nested within the rotary dial 130 and is marked to receive medication. The connector typically includes a conduit member (tubing) that is surrounded by a skirt member or the like that mates with the outer hub of the syringe barrel. A flange or diaphragm can be provided for hermetically sealing with the syringe barrel (outer hub).

Figure 10:
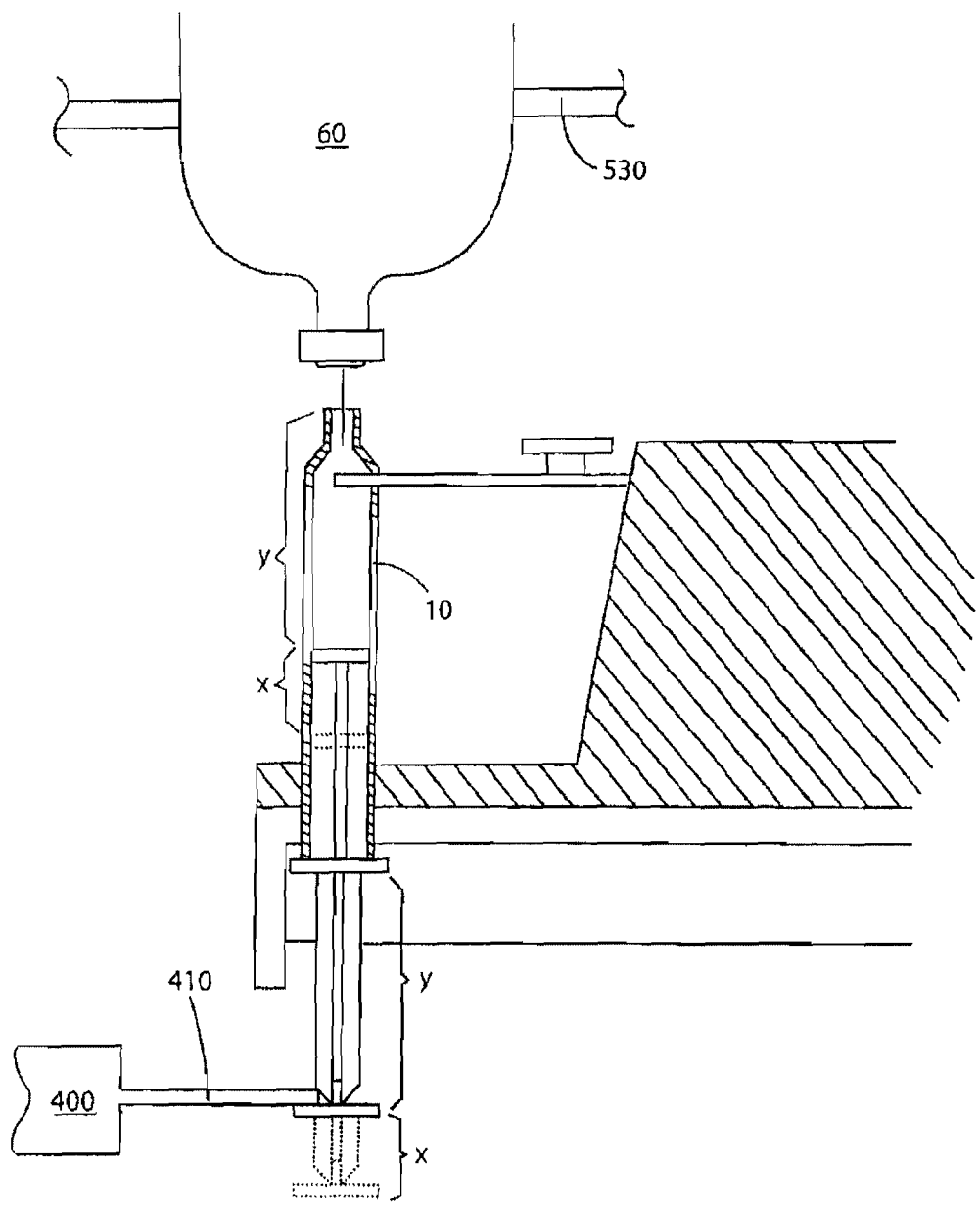
FIG. 10 is a cross-sectional view of drug delivery directly from a drug vial by extending the plunger of a syringe with an automated mechanism.

In commonly assigned U.S. patent Ser. No. 11/434,850 (which is hereby incorporated by reference in its entirety), it is described how the plunger 50 of the syringe 10 can be extended with precision to a prescribed distance in that application, the plunger 50 is extended to create a precise volume in the barrel that is to receive a precise prescribed dosage of medication that is injected therein at a downstream location. However, it will be appreciated that the action of extending the plunger 50 can serve more than this purpose since the extension of the plunger 50 creates negative pressure within the syringe barrel and thus can serve to draw a fluid therein. For example, once the connector is sealingly mated with the open syringe tip end, the medication source (e.g., an IV bag) is fluidly connected to the syringe 10 and thus can be drawn into the syringe barrel by means of the extension of the plunger 50. In other words, the plunger 50 is pulled a precise distance that results in the correct size cavity being opened up in the barrel for receiving the fluid but also the extension of the plunger creates enough negative pressure to cause the medication to be drawn into the syringe barrel. This is thus an alternative means for withdrawing the proper amount of medication from a member (in this case the source) and transferring the desired, precise amount of medication to the syringe 10. The operation of this alternative embodiment can be referred to as operating the system in reservoir mode and is shown in FIG. 10. One advantage of this embodiment is that multiple syringe drivers or the like or some type of pump mechanism are not needed to pump the medication into the syringe 10 but rather the drawing action is created right at the rotary dial 130. This design is thus fairly simple; however, it is not suitable for instances where drug reconstitution is necessary. FIGS. 6 and 10 illustrate a reservoir mode station 770 where equipment related to the reservoir mode of operation is provided.

It will also be appreciated that the source does not have to be a medication source in that it does not have to contain an active drug but instead, the source can contain diluent that is to be drawn in a prescribed volume into the syringe, especially for purposes of serial dilution, as described below. More specifically and as illustrated in FIGS. 1 and 6, in the reservoir mode (station 770), the fluid source can consist of a number of drug delivery bags 750 that are already filled either premixed medication or with only diluent that is later used to dilute medication as described in detail below. The filled drug delivery bags (e.g., IV bags) 750 can be hung in a select area, with each bag 750 having an outlet conduit through which the fluid contained in the bag is drawn. It will be appreciated that the outlet conduits associated with the drug delivery bags 750 can be interconnected as by connecting each of the bag outlet conduits to a common line 754 with one or more valves or the like being used to selectively control which bag outlet line is in directly fluid communication with the common line 754. In this manner, a number of different medications can be hung and be ready for use and the user of the system merely has manipulate the valve (either manually or automatically using a computer, etc.) to connect the selected bag 750 to the common line 754.

The computer that operates the entire system can be in communication with the valves to permit and to control the flow of the prescribed desired fluid from one bag 750 to the common line 754. The common line 754 is thus in communication at a first end with the outlet conduit of the select bag 750 that contains the desired fluid and another end of the common line 754 is configured to mate with a syringe inlet port to permit the fluid in the bag 750 to be drawn into the bag by extending the plunger 50 a predetermined distance as described above to cause a precise, target volume of fluid to be drawn into the barrel of the syringe 10. For example, the free end of the common line (conduit) 754 can contain a connector or adapter (e.g., a stopper element) 760 that is configured to mate with the inlet opening (port) of the syringe barrel in a sealed manner. Since it is the extension of the plunger 50 that generates the means of drawing a prescribed volume of fluid into the syringe barrel, the connection between the end of the common line (e.g., the connector thereof) and the syringe barrel is such that the creation of negative pressure in the syringe barrel 20 causes the fluid to be drawn into the barrel. In other words, it is desirable to establish a seal or the like between the end of the common line 754 and the syringe barrel so that negative pressure can be established and maintained in the syringe barrel.

For purpose of illustration, the delivery of fluid from one source during operation of the reservoir mode to one syringe 10 is performed at the reservoir mode fluid delivery station 770 that is arranged relative to the other stations of the system 100.

According to one embodiment, the free end of the common line 754 is secured to a controllable, movable device, 765 such as a robotic arm or an automated arm, that can be controllably moved. In particular, the movable device is moved vertically at least along a linear axis so as to drive the free end of the common line 754 (the connector) into a sealed coupling with the syringe barrel when it is driven in one direction or when it is driven in the opposite direction, the common line disengages from the barrel of the syringe 10 to permit the syringe to be advanced to another station, such as the fluid transfer station 170 described above where reconstituted drug can be delivered into a syringe 10 that was previously injected with fluid through the common line 754 from the fluid source when operating in reservoir mode.

It will be appreciated that the reservoir drug delivery station 770 and the fluid transfer station 170 are different stations that are located at different locations, such as adjacent stations along the dial 130.

The capped syringe 10 can then be transferred to other stations, such as a station where the syringe in bandolier form is cut into individual syringes 10 that are labeled for particular patients. The syringes 10 can then be unloaded from the dial 130 and then further processed, as for example, by being delivered to a storage receptacle where it is stored or by being delivered to a transporting device for delivery to the patient or the filled syringes 10 can be cataloged and packaged in different boxes or the like for delivery to one or more locations. For example, in a batch type process, which is typically more common with the reservoir mode type of operation, a number of syringes 10 can be prepared and delivered into a single box or receptacle.

Figure 8:
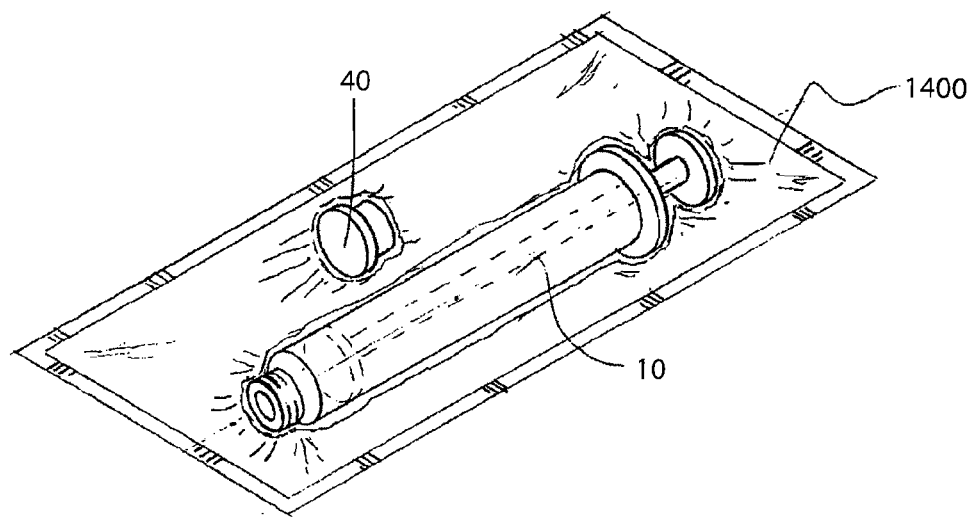
FIG. 8 is a perspective view of a syringe with its cap removed contained in a sealed package.
Figure 9:
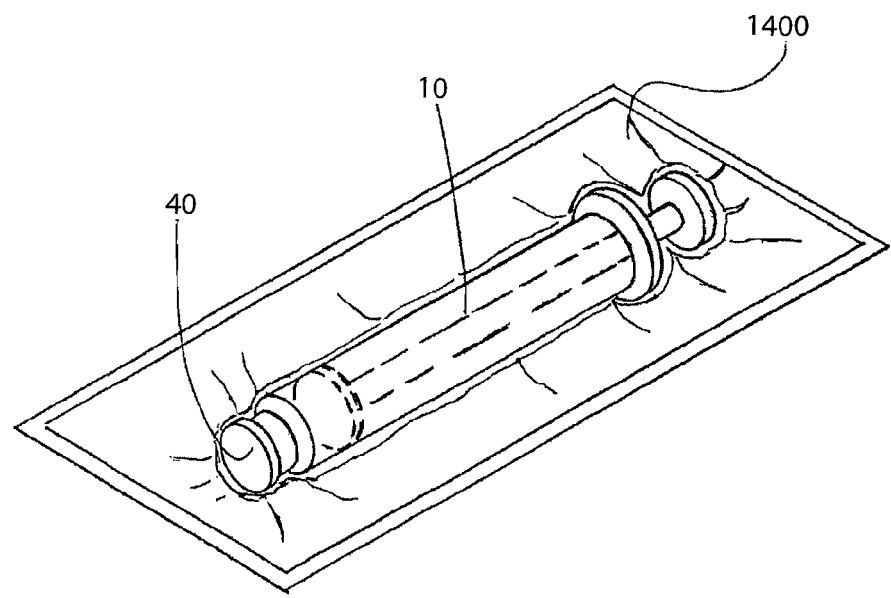
FIG. 9 is a perspective view of a syringe with it cap attached contained in a sealed package.
Figure 19:
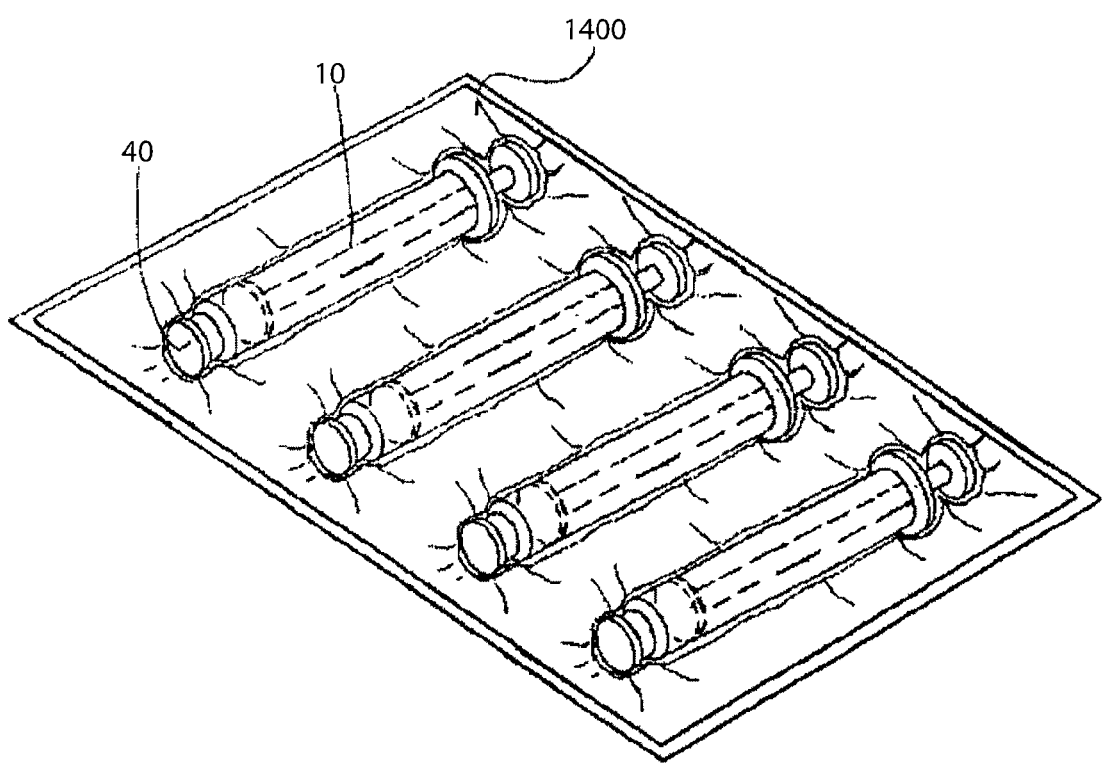
FIG. 19 is a perspective view of multiple syringes with their respective caps attached thereto contained in a singe sealed package.

In another aspect, the syringes 10 can be initially supplied in a sealed, sterile bag 1400 as shown in FIGS. 8 and 9. In this embodiment, the syringe 10 includes the cap 40 which can either be attached to the barrel (FIG. 9) or it can be off the barrel (FIG. 8) and supplied next to the barrel and plunger which are coupled together in the sterile bag 1400. The syringe 10, including the cap 40, is thus stored in a sterile environment before being used in the automated drug preparation system 100. FIG. 19 is another embodiment showing a single sterile bag 1400 that contains a plurality of capped syringes (bulk bag). The individual syringes are preferably not attached to one another but are held in the sealed bag in a loose, detached state so as to be easily accessible for presentation to a sorting and loading mechanism that is constructed to individually feed the syringes to the transport device 130.

More specifically, the syringes 10 can be loaded onto the device at station 120 and the cap 40 can either be manually or automatically put onto the barrel of the syringe prior to or at station 120. For example, an automated device can grip and place the cap 40 on the barrel before the syringe 10 is loaded onto the dial 130 or the automated gripper device can grip the cap 40 and place the cap on the post 161 of the dial 130. The system 100 is then operated in the manner described herein which results in the cap 40 being placed back onto the syringe 10 at a station after either the drug delivery station 170 or the reservoir mode station 770.

It will therefore be appreciated that the same cap 40 that was present in the sterile bag 1400 at the beginning of the loading process can be the same one that is attached to the filled syringe 10 at the end of the process. This is in contrast to traditional design where a syringe that is contained in the sterile bag 1400 can be capped with a temporary cover or cap-like structure; however, after the bag is opened and the syringe is removed, this cover or cap-like structure is intended to be discarded since it is not intended to function as a cap member that seals the barrel. In other words, this cover that is contained in the sterile bag is not used later in the automated drug delivery system for covering the syringe. The system of the present invention thus reduces waste since the cap member in the sealed bag is used.

In yet another aspect, the fluid volume of a fluid contained in a receptacle, such as a vial or syringe, can be measured using a number of different means. For example, U.S. Patent Application Publication No. 2006/0178578, which is hereby incorporated by reference in its entirety, discloses a system and method for calculating a volume of liquid that is disposed within a container. In addition, the fluid volume can be measured with a laser light source.

A small laser is used to generate a line source and the light line is projected through the container (e.g., a syringe) parallel to the long axis of the syringe. When the laser light passes through the fluid, which is primarily composed of water and drug, the light bends due to refraction. The index of refraction is 1.38 for water verses approximately 1.0 for air. By using a laser to construct a small light beam, which intersects the vial or syringe, the air/fluid boundary can be easily detected using the difference in index of refraction between water and the fluid. Once the boundary is located, the syringe volume can be calibrated to the pixel location. A method based on using a second order polynomial is disclosed in the '578 publication and is also suitable for use in the present method of using a laser light source.

The light source is relatively simple and can be a laser diode with a "line lens" that is used to illuminate the test object. Any light source that produces a line along the syringe can be used, e.g., a backlight with a slit mask. The laser image can be projected onto a label which wraps most of the cylinder of the vial and this allows volume estimation when the liquid if not visible through the label.

Figure 12A:
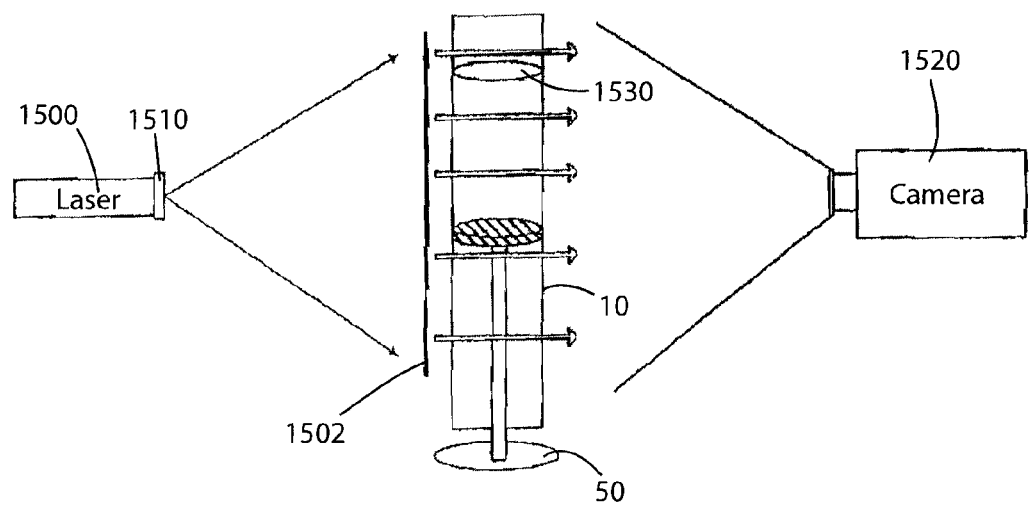
Figure 12B:
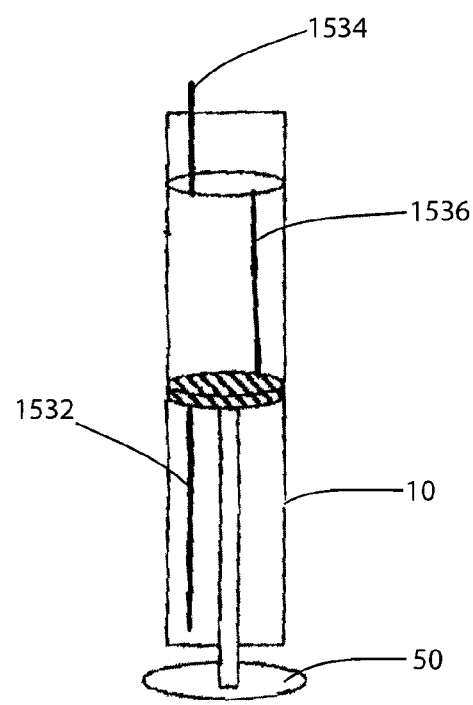
FIG. 12B is a side cross-sectional view of a camera view of the syringe with an offset laser line that represents the location of the liquid.

As shown in FIGS. 12A and 12B, syringe 10, with plunger 50, is illustrated. A laser 1500 is provided and is equipped with a line generator lens 1510, that is arranged so that it is directed toward the syringe 10. A camera 1520 is provided on the opposite side of the syringe 10 opposite the laser 1500. The syringe 10 contains a fluid solution (e.g., fluid medication) and there is a liquid/air meniscus 1530 and the plunger 50 is also illustrated and its position can be determined. It will be appreciated that below the plunger 50, there is no liquid.

As shown in FIGS. 12A and 12B, the projected laser line 1502 passes through the syringe 10 and the line is refracted where there is liquid (the dosage of medication) as opposed to where there is air both above the liquid/air meniscus and below the plunger 50. The camera view of the syringe 10 is shown in FIG. 12B with an offset in the laser line due to the index of refraction when the light passes through the liquid. As shown in FIG. 12B, there are two laser line segments 1532, 1534 that are linear with respect to one another and one laser line segment 1536 that is offset from the other line segments 1532, 1534. Once this segment is determined where the liquid is present, the volume can be determined using the process described in the '578 publication.

Thus, one exemplary method of measuring a liquid volume of medication contained in a syringe includes the steps of: (1) generating a light beam in the form of a laser line from a laser; (2) directing the light line towards the syringe; (3) positioning a camera proximate the container on an opposite side relative to the laser; (4) passing the laser line through the container such the line is refracted where there is liquid as opposed to air both above a liquid/air meniscus and below a plunger of the syringe; (5) calibrating the volume of the medication to pixel locations and map boundary locations of the refracted laser line segment; and (6) calculating the liquid volume based on the calibration and location and boundaries of the refracted laser line segment that represents where the medication is present.

Figure 13:
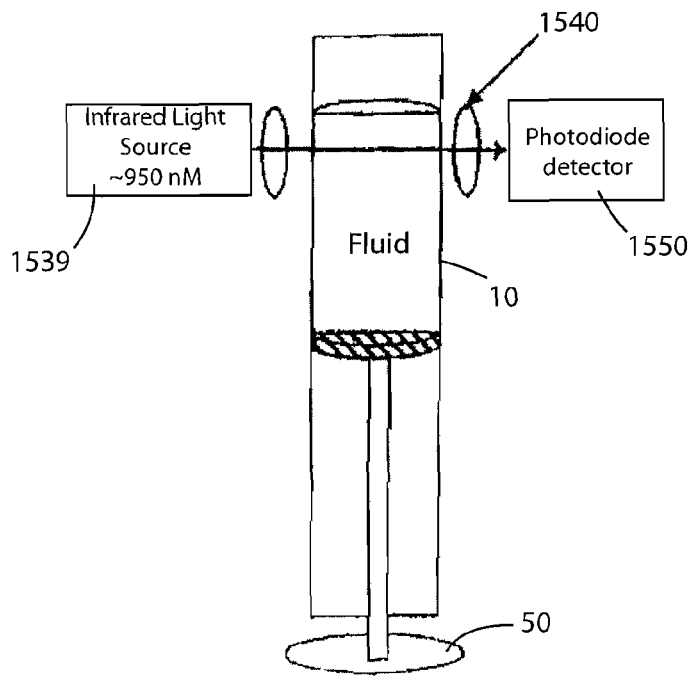
FIG. 13 is a side cross-sectional view of an apparatus for measuring fluid level by water absorbance.

In yet another aspect, the fluid level can be measured by water absorbance as shown in FIG. 13. Since the liquid in most drugs is essentially water and the liquid is clear, it is difficult to sense when the liquid level has reached an electronic sensor. Insignificant light is absorbed through water in the visible spectrum but water has an absorbance peak near 970 nanometers (infrared spectrum). When light at that wavelength is passed through a syringe once can measure the attenuation from the following formula:

Absorbance=$-\log(I_0/I)$, where $I_0$=initial intensity and I=transmitted intensity. FIG. 13 shows an exemplary set up to measure the fluid level in this manner and in particular, the syringe 10 with plunger 50 extended contains a liquid medication and an infrared light source 1539 is provided and is directed towards the syringe 10 so that is passes through the liquid contained in the syringe 10. A collimating lens 1540 can be used to collect more light through the syringe field of view and then concentrate the light at the local point of the lens 1540 and a detector 1550, such as a photodiode detector, is used to measure the absorbance signal when there is no liquid verses a syringe filled with a liquid (e.g., the liquid medication).

Figure 14:
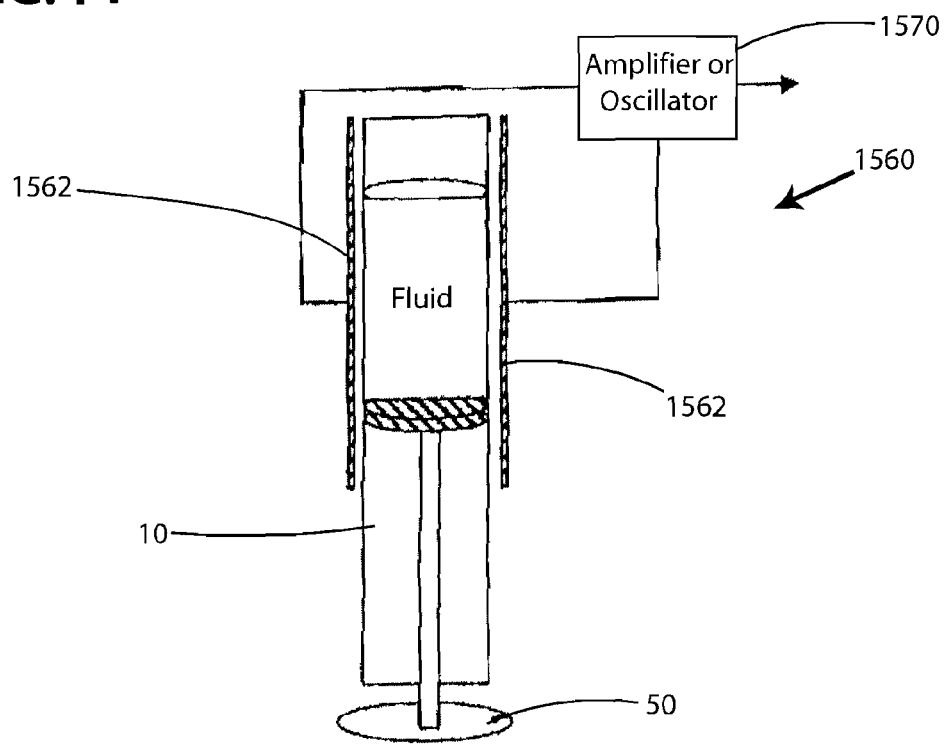
FIG. 14 is a side cross-sectional view of an apparatus for measuring fluid volume by capacitive sensors.

In yet another embodiment, the fluid volume is measured by a capacitive sensor, generally indicated at 1560 in FIG. 14. The capacitor sensor 1560 is created by using parallel plates 1562 on the sides of the syringe 10. The capacitance measured between the plates 1562 is proportional to the dielectric constant of the fluid in the syringe 10. The dielectric constant of water is approximately 80. The dielectric constant of air is 1. As the liquid fills the syringe 10 with liquid, the capacitance rises and is proportional to the volume of fluid in the syringe 10. In particular:

$C=(E_o*E_r*A)/d$; where C is the capacitance in Farads; $E_o$ is the permittivity of free space; $E_r$ is the dielectric constant of the insulator (air or water); A is the area of each capacitor plate 1562; and d is the separation of the plates 1562. An amplifier or oscillator 1570 is used to product an analog signal proportional to the variation in capacitance.

In another aspect, the fluid level can be measured with a camera 1580 at the top of the syringe 10 as illustrated in FIG. 15. As the liquid is delivered to the syringe 10 and prior to the liquid touching the top of the syringe 10, air bubbles are present. In contrast, once the liquid has completed filling the syringe 10, the air bubbles are eliminated or very few in number. Thus, the camera 1580 that is directed towards the top of the syringe 10 can monitor the change in appearance at the top of the syringe in order to measure the fluid level of the syringe 10.

It will be understood that the integrity and accuracy of any of the fluid filling stations of the system 100 can be checked by using a laser beam of light in order to detect a fill volume within a syringe or some other container. In addition, the system 100, in this embodiment, is configured to adjust the filling process at the point of filling in the event that the expected amount of fluid was not transferred. For example, at station 770, when the syringe plunger 50 is extended to draw in diluent or other fluid, the a laser beam or other source of light is positioned at the target fill location and if the fill volume does not "break" (impinge) this laser line, then the controller will instruct the automated fluid delivery system to deliver additional fluid (preferably in small increments) until the total fill volume breaks the laser line at which time the fluid delivery is terminated.

The use of a laser to detect the fill volume can be used at the point of reconstitution where the reconstituted medication is delivered to the syringe 10 or it can be used at the point of transferring the medication to a syringe at some other location or it can be used at station 770 (in reservoir mode) when diluent or pre-made medication or some other fluid is delivered to the syringe 10 by extending the plunger 50 and in this case, if the expected amount of fluid was not transferred, then the device 400 that extends the plunger 50 is further activated to cause further movement of the plunger 50 to cause an incremental amount of additional fluid to be drawn into the syringe 10.

It will also be appreciated that a number of other safety features can be present and incorporated into the system 100. For example, sensors can be provided at any number of the various stations of the system 100. In particular, a sensor can be provided at the load station 120 where drug delivery devices, such as syringes, are initially loaded into the system for monitoring and indicating when no more syringes 10 are present for loading into the system 100. For example, if the feed of syringes 10 is interrupted or if the system 100 simply runs out of syringes 10, the sensor recognizes this event and sends an alert signal to the master controller. Any number of different types of sensor devices can be used to accomplish this result and in particular, the sensor can be a weight based sensor that detects the weight of an object (syringe) or it can be a device that visually detects the presence of an object (syringe).

Other sensors are provided to detect other conditions or events in the system 100 and in particular, the fluid sources 750 (e.g., hanging IV bags) that are used in the reservoir mode of operation at the station 770 can each includes a sensor that monitors the fluid level of the respective source 750 and in the event that a low fluid level is detected, the sensor sends an alert signal to the master controller identifying that a low fluid level has been detected at one particular source 750. The fluid sources 750 typically include diluent for use in reconstituting the drug at station 170; however, one or more of the sources 730 can contain other fluids besides diluent.

Other sensors include sensors which monitor the condition of the syringe 10 as it is loaded onto the dial 130 and in particular, the sensor monitors whether or not the cap 40 is present on the syringe 10 since if the cap 40 is missing from the syringe 10, the sterility of the syringe 10 may be compromised and therefore, the syringe 10 is removed for further inspection or is discarded. Another type of sensor is a reader that reads the barcode that is part of the label of the syringe 10 to make sure that the label is legible and the act of labeling was completed properly.

Figure 16:
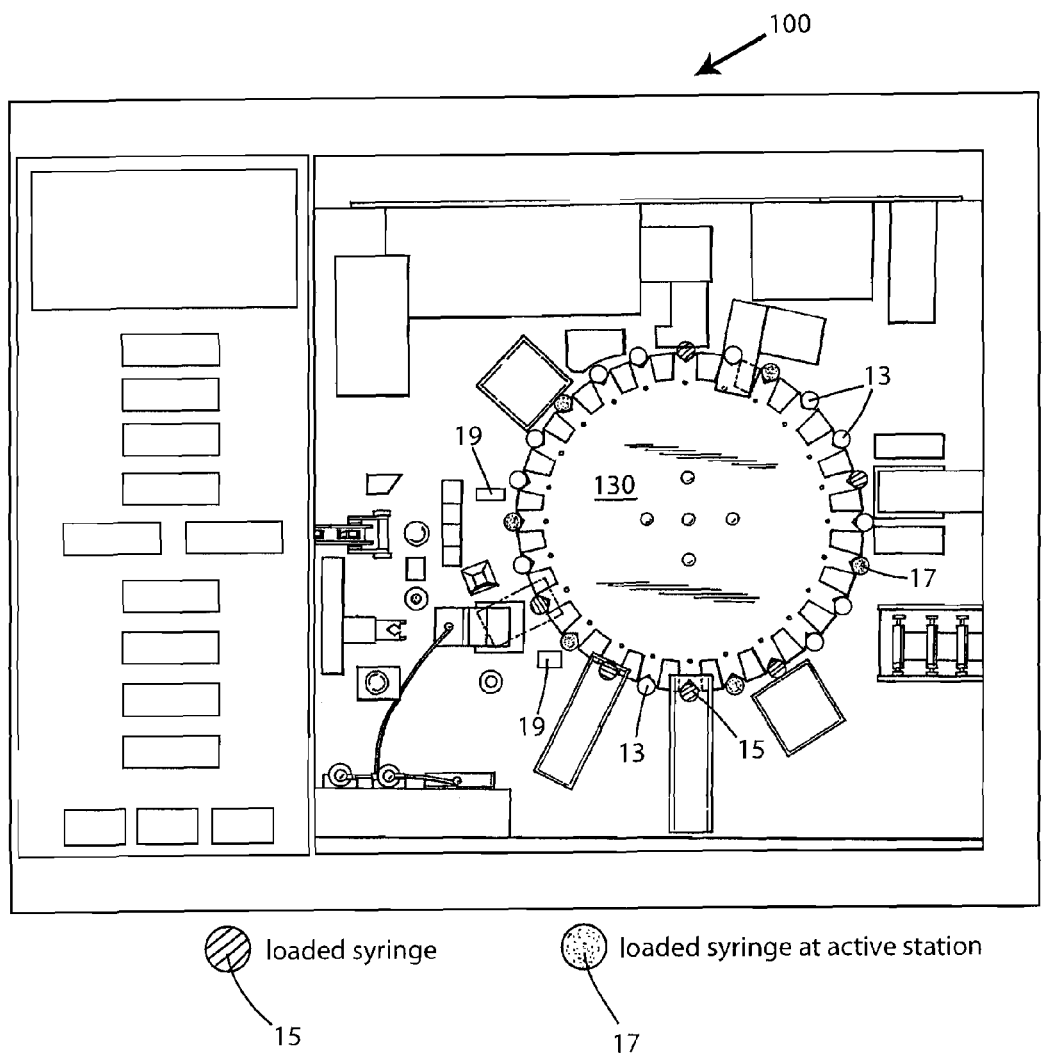
FIG. 16 is a computer screen image of the system of FIG. 2 with indicia representing loaded stations and empty station and active and inactive stations.

In yet another feature of one embodiment of the present invention, the system 100 can include software that includes a computer display that permits the operator to easily determine at any given time the location and status of each syringe 10 as it advances through the automated system as illustrated in FIG. 16. In particular, the system 100 has a video display 1001 that displays the movements of the components of the system 100 in real time so that the user can monitor and track the drug delivery devices (e.g., syringes or bags) as they are advanced from one station to a next station. For example, the system 100 typically includes a keyboard or pad or the like that permits the operator to input certain data, such as, the drug order contents, the drug vial information, etc., and it includes a display or monitor that permits the operator to graphically view all this information in real time.

FIG. 16 is a screen shot or image of an exemplary video display in which the various stations of the system 100 are identified, as well as the conveyor or transporter (in this case, the dial 13), that moves the drug delivery devices. In particular, the precise locations of the syringes around the dial 130 are indicated by a closed circle outline 13 in FIG. 16, however, it will be appreciated that other shapes can equally be used to illustrate the location of the syringes 10. As will be appreciated, these circle outlines 13 represent pockets or nests around the dial 130 where the syringes 10 are inserted and held in place as the dial 130 is advanced to move the syringes from one location to another location.

If a particular pocket or nest is empty and does not include a syringe 10, then the circle outline 13 at this location remains empty and is not "filled" with color so as to indicate the presence of a syringe 10. When a syringe 10 is fed into and held within a particular pocket or nest, the circle is shown as a filled circle 15 of any given first color. In this manner, the empty circle identifiers 13 around the dial 130 represent areas where no syringe is present and the filled circle 15 identifiers represent locations where syringes 10 are present.

In another aspect, the color of the filled circles 13 can change based on whether the syringe that is located at this particular location is undergoing some type of operation and is thus, at an active station or whether, the syringe 10 at this location is inactive and is waiting to be advanced to a next station where an operation is to be performed. For example, a loaded inactive syringe 10 can be identified on the screen by a blue colored circle 15 and when this loaded syringe 10 is advanced to an active station where some type of operation is performed on the syringe (e.g., decapping of the syringe, filling or aspiration of medication, etc.), the color of the circle 13 changes from blue to green to indicate that this particular syringe is at an active station and is being subjected to some type of operation. This is represented as a green colored circle 17. As soon as the operation has stopped, the color of the circle 13 returns back to blue to indicate an inactive site.

It will also be appreciated that each syringe 10 can be identified by a tag 19 on the display screen that contains a unique identifying code to permit the operator to easily and quickly determine which syringe 10 is located at each station. For example, the tag 19 can be visual tag that is displayed on the screen next to the circle 13 that identifies a loaded syringe and as the transporter (dial) is advanced, the tag 19 moves along with the depiction of the syringe (e.g., the filled-in circle identifier). The unique identifying code can be chosen by the computer software and linked to the syringe barcode, etc., or the identifying code can be the barcode itself.

In contrast to conventional automated syringe handling systems, the system 100 is not restricted to being operated in a sequential manner where one syringe is fed from one station to the next but instead, the system 100 is configured so that there can be a number of active work stations performing some type of automated operation at the same time. Thus, at any given time, the video display can show two or more green colored syringe identifiers to indicate that two or more syringes are at active stations where work is occurring. For example, in the serial dilution mode of operation, both the reservoir mode station 770 and the fluid transfer station 170 can be and preferably are active at any one point in time and therefore, the visual syringe identifiers at these two stations will be colored green on the visual display to show that work is being performed on these syringes at the given stations. In addition, one syringe may be undergoing a decapping operation at station 150, while at the same time, another syringe is receiving a dosage of medication at the fluid transfer station 170 and therefore, the visual syringe identifiers for these two syringes will be green colored. It will be appreciated that there is no limit as to the number of stations that can be active at the same point in time and therefore, in contrast, to conventional design, the present invention is a multi-station operation that is not limited to being a sequential operation where a gripper or robotic device delivers one syringe from one station to another station until all operations have been performed on the syringe and then at that point in time, the robotic device will get another empty syringe and start the sequential process over. However, this type of process is a sequential process where only after work is completed on one syringe does work start on the next syringe.

Figure 17:
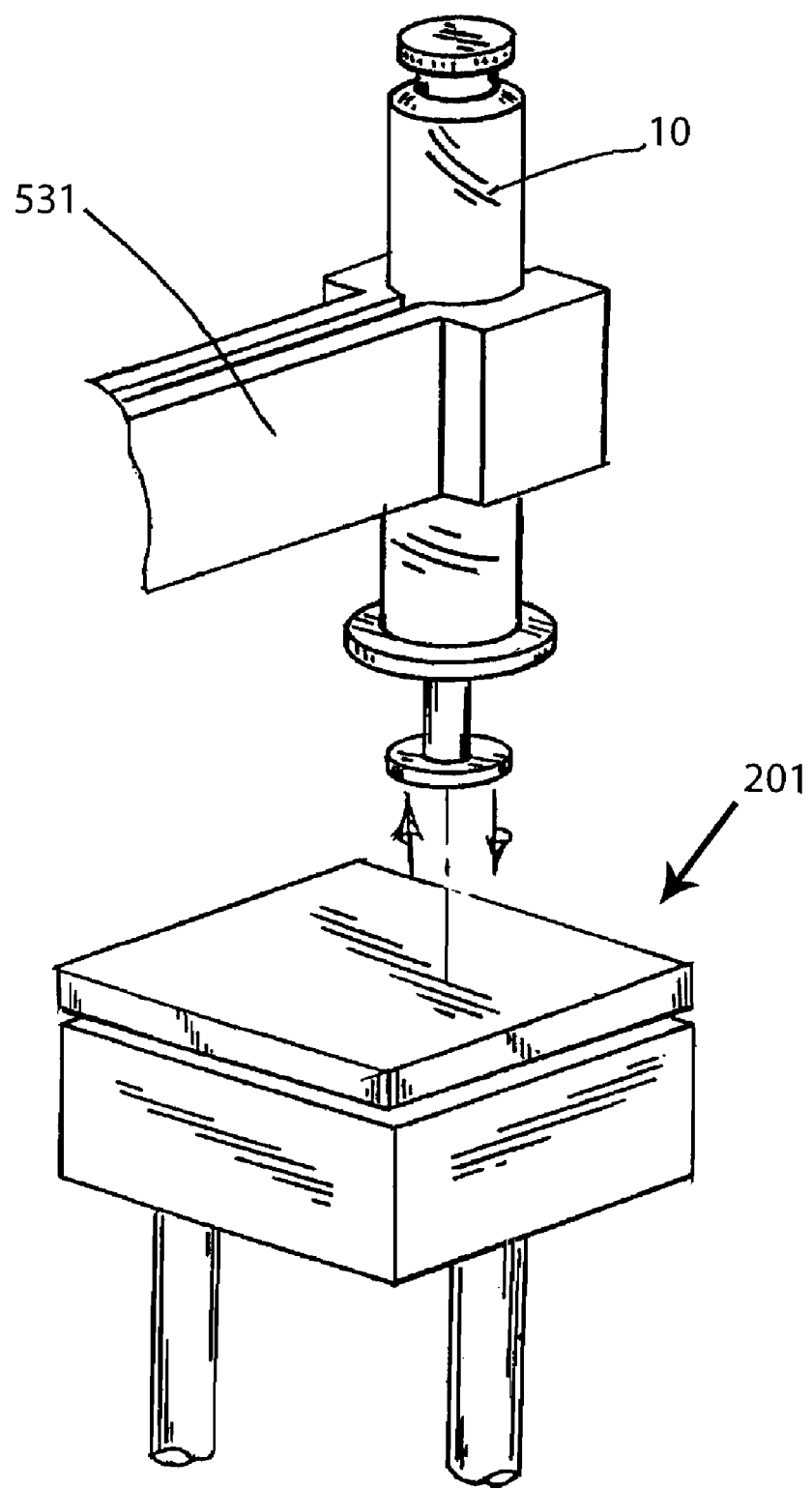
FIG. 17 is a partial perspective view of a robotic device holding a syringe and a weight station for weighing a filled syringe.

In yet another safety feature of the present invention illustrated in FIGS. 2 and 17, syringes that are present at a set interval are removed from the dial 130 just prior to the unloading station 200 and are delivered via a robotic device 531 to a weigh station 201 where the filled syringe is weighed. For example, every $10^{th}$ syringe or some other syringe interval can be removed from the dial 130 and delivered to the weigh station 201. The filled syringe 10 is then checked with a stored value (target value) and if it is within a range of accepted values, the syringe is then delivered back to the unloading station where it is then removed from the dial 130 and placed on a conveyor or the like. This safety feature is particularly useful and is intended for use more when a batch of syringes having the same specifications is prepared since checking syringes at predetermined intervals is a quality control measurement for checking the integrity and precision of the batch filling devices.

The software can be configured so that if one of the selected syringes has a weight that is outside of the acceptable range, then not only is this particular syringe discarded but the operator can be given several safety feature options, including, modifying the interval at which the syringes are checked so that the interval is decreased (e.g., instead of checking every $10^{th}$ syringe, the system can be modified to check every $3^{rd}$ syringe, etc.); the operator can undertake a check of the filled syringes that exited the system 100 for a given preceding time period; etc.

As shown in FIG. 1, the system 100 is typically incorporated into the housing 1300, such as a cabinet, that has different compartments for storing the components of the system 100. For example and as shown in FIG. 1, the housing can include a first space 1310 in the form of the drug cabinet 110 that stores the drug vials 60 (FIG. 6), as by storing them vertically in a number of different rows. The drug cabinet 110 preferably includes sensors and the like for indicating when a row of drug vials 60 is low or has run out. The mechanism 510 (FIG. 2) that transports an individual drug vial 60 from the drug cabinet 110 to the other working components that are located in a second space 1320 of the housing 1300 is located along one side of the housing 1300.

The other working components of the system 100 that are disposed in the second space 1320 are accessible through one or more side windows 1322 and preferably, each side of the housing 1300 includes slideable doors or windows 1322. When the doors 1322 are shut, the interior of the housing 1300 is sealed. Since a number, if not all, applications, especially, the preparation of chemotherapy drugs, require a sterile environment, the housing 1300 includes one or more filters 1332 and in particular, one or more HEPA filters 1332 (high efficiency particulate absorbing filters) that are typically designed to remove at least 99.97% of dust, pollen, mold, bacteria and any airborne particles with a size of 0.3 micrometers at 85 liters per minute.

In one embodiment, the housing 1300 has the HEPA filtration system 1332 incorporated into a ceiling or roof 1340 of the housing 1300 and includes one or more HEPA filters 1332. The HEPA filter 1332 functions to filter air that enters the cabinet by any number of different means, including the opening of one glass door 1322. The HEPA filtration system 1332 also includes at least one and preferably a plurality of sensors/sensing devices, such as particulate sensors, 1350 that continuously monitor the conditions inside the housing 1300 and more specifically, measure the level of particulates within the housing 1300. The sensors 1350 can be placed in a number of different target locations within the housing 1300. For example, one sensor 1350 can be located on the ceiling/ roof one can be located on a side wall of the housing, one can be located on a floor of the second space, etc.

The sensors 1350 communicate with the master controller which is configured to continuously monitor the readings from the sensors and if one reading, such as particulate count, is outside an acceptable range, then the master controller takes appropriate action which can be to alert the operator and/or take remedial action in an attempt to correct the matter. For example, the alert can be in the form of an alarm (audible and/or visual) that alerts the operator that an error or undesired condition exists in the housing or with the system 100. The alert can also be in the form of a text message, such as an email, that is sent to one or more recipients to alert them of the current unacceptable condition. Conventional wireless or wired communications equipment can be provided to perform this function.

The alert functionality and error display functionality is not limited to instances where a high particulate count is observed but it can be a result of any other type of error situation, including a jam at the loading station 120 or that the machine has run out of a feed of syringes 10 or a jam has occurred at another station or a measured parameter is outside an acceptable range.

In one embodiment, the housing 1300 includes a visual alert device 1352, such as a flashing light or solid color light, that is positioned near the top of the housing so that anyone in the area of the housing 1300 can see when it is activated and is flashing to alert the operator to check the visual display (computer monitor) for an error message that details what problem or error has been detected. For example, during normal operation, the light 1352 is a green color; however, when there is a problem or error, the light 1352 has a red color and can also blink, etc., or remain a solid color.

Once the light 1352 flashes, the operator can ascertain the reason for the activation of the light by looking at the computer screen since preferably, there is a section (e.g., a lower portion of the screen) that lists any current error message. For example, the display could indicate "Error Message 002—Jam at Syringe Feed Station" or "Error Message 005—High Particulate Reading at Sensor 001" or "Error Message 006—Syringe Cap not detected at Station 0033," etc. Proper remedial action can then be taken.

In yet another safety feature, the drug cabinet 110 can be constructed so that is can receive a cleaning solution that is intended to decontaminate the drug cabinet 110. For example, any wiring that is exposed in the drug cabinet 110 can be routed through protective sleeves or is otherwise protected and the drug cabinet 110 can include one or more devices that are intended to dispense fluid in a controlled manner through the drug cabinet, including the drug vials 60, contained therein. For example, the devices can be in the form of misting devices or sprayers that are fluidly connected to both a source of decontaminating fluid and a controller that controls the dispensing of the fluid. The controller is operatively connected to the master controller (computer) and therefore is a programmable device that can be programmed to dispense fluid at regular intervals. For example and depending upon applicable regulatory requirements, the controller can be set up to cause a spraying of decontaminating fluid within the drug cabinet 110, including over the stored drug vials 60, at a precise time interval, such as daily, weekly, monthly, etc. and for a programmable amount of time.

Any number of different decontaminating fluids can be used with one exemplary embodiment being alcohol.

The drug cabinet 110 can thus contain a drain or the like to collect any decontaminating fluid that may have run off the equipment in the drug cabinet, including the vials. The drain can then lead to a waste receptacle.

Figure 18:
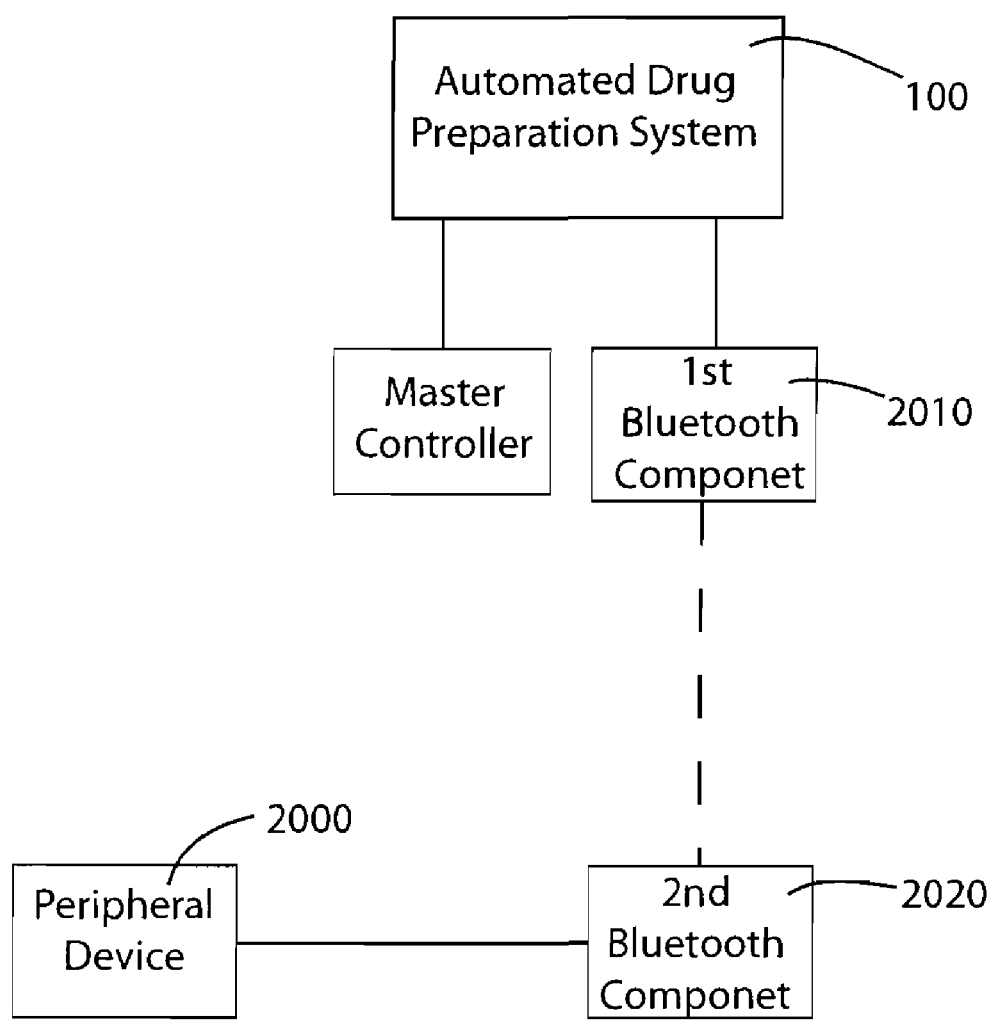
FIG. 18 is a schematic view of a Bluetooth communications network incorporated in the system of FIG. 1 and a remote peripheral device.

In yet another aspect of the present invention and as shown in FIG. 18, the system 100 is configured to communicate with a remote peripheral device 2000 and in particular, the system 100 is alerted by the peripheral device 2000 when a malfunction or other undesirable condition exists at the peripheral device 2000. The peripheral device 2000 can be any number of different types of devices that perform a desired function for the system 100. For example, the peripheral device 2000 can be in the form of a syringe bagger that operates to bag or otherwise place each syringe in an enclosure; however, there are other remote devices that can be used. In general, the peripheral device 2000 can be any number of different types of devices that are designed to be placed in a remote location and cooperate with the controller of the system. For example, the device 2000 is not limited to being a packing machine but instead can be in the form of a remote printer or other electronic device that performs some type of operation with respect to the drug product.

One exemplary bagger 2000 is commercially available from the Automated Packaging Systems under the trade name Autobag® AB 145™ Bagger, which is a packaging automation system that fills and seals bags that are provided on a roll.

There are a number of different techniques that can be used to connect electronic devices to one another. For example, component cables, electrical wires, Ethernet cables, Wifi, infrared signals, etc., can be used to connect the devices. One of the disadvantages with a hard-wire connection is that such a connection poses safety hazards both to the operator and the system 100.

Since it is desired that the device 2000 be remote from the other components of the system 100, the means for communication between the remote device 2000 and the controller of the system 100 should be such that the device 2000 can be in wireless communication with the controller. For example, one exemplary means of communication is in the form of Bluetooth communication network. Bluetooth is essentially a networking standard that works at two levels: (1) it provides agreement at the physical level (Bluetooth is a radio-frequency standard); and (2) it provides agreement at the protocol level where products have to agree on when bits are sent, how many will be sent at a time, and how the parties in a conversation can be sure that the message received is the same as the message sent.

Advantages of Bluetooth are that it is wireless, inexpensive and automatic and it does not suffer from the disadvantages of using infrared communication. Bluetooth networking transmits data via low-power radio waves. It communicates on a frequency of 2.45 gigahertz (more specifically, between 2.402 GHz and 2.480 GHz). One of the ways Bluetooth devices avoid interfering with other systems is by sending out very weak signals of about 1 milliwatt. The low power limits the range of a Bluetooth device to about 10 meters (32 feet), thus cutting the chances of interference between the associated computer system and other devices, such as a portable phone or television. Even with the low power, Bluetooth doesn't require line of sight between communicating devices.

When Bluetooth-capable devices come within range of one another, an electronic conversation takes place to determine whether the devices have data to share or whether one needs to control the other. The user does not have to press a button or give a command; instead, the electronic conversation happens automatically. Once the conversation has occurred, the devices form a network. Bluetooth systems create a personal-area network (PAN) or piconet.

According to one exemplary embodiment, a pair of Bluetooth devices (components) 2010, 2020 are used to alert the system 100 as to the status of the peripheral device 2000. For example, when the peripheral device 2000 is in the form of a bagger, the Bluetooth devices 2010, 2020 can be used to alert the system 100 that a malfunction has occurred at the device 2000. Based on the alert or indication that an error has occurred, the system 100 performs certain actions to remedy the situation. In one exemplary embodiment, the present arrangement ensures complete electrical isolation between the system 100 and the device 2000, with Bluetooth technology being selected as the wireless communication medium between the system 100 and the device 2000 through which the error state is communicated for action.

As shown in FIG. 18, one USB Bluetooth serial dongle 2010 is placed in one of the available USB ports on the system 100. The USB Bluetooth dongle 2010 is powered by a personal computer, etc., (e.g., the controller of the system 100) and wireless communication is available as soon as a user logs onto the personal computer of the system 100. The second Bluetooth dongle 2020 is of a serial type and is placed on the device 2000 (e.g., syringe bagger). Power is applied to the serial dongle 2020 through Pin 9 when the peripheral device 2000 is on and in a functioning state and when the peripheral device 2000 enters a malfunction state (or there is a change in its state), the serial dongle 2020 is immediately powered off. This state change of the peripheral device 2000 generates a reaction/response from the system 100. After the operator investigates the problem and the peripheral device 2000 is reset, power is again applied to the serial dongle 2020.

In situations where Bluetooth is used to replace physical cables for RS-232 communication, a virtual serial port must be utilized. By assigning a virtual serial port to the serial dongle 2020, the system 100 gains the ability to automatically connect both Bluetooth devices when the port is opened by the software. If two Bluetooth devices are connected, any data sent between the two devices which does not adhere to the proper command format is echoed back to the sending Bluetooth device. The system 100 uses the virtual communications port, provided by a BlueSoleil software application, to send an arbitrary ASCII character to the serial dongle 2020. If a connection is established, the character is echoed back, the serial dongle 202 is powered off, indicating an error (malfunction) with the peripheral device 2000 (e.g., bagger device). The remote device 2000, in this case, the bagger, does not contain any circuitry to control the communications between the two Bluetooth devices 2010, 2020, but simply powers the device 2000 off when an error exists. The software of the system 100 checks the status of the Bluetooth connection before each syringe is dropped onto the output conveyor. If a bagger malfunction error is detected, the appropriate error handling routine is executed. This concept provides the ability to communicate any binary situation wirelessly between the two devices without control circuitry on the remote side.

In one embodiment, the Bluetooth device 2010 is in the form of a Bluetooth USB adapter that is manufactured by Cambridge Silicon Radio and the Bluetooth device 2020 is in the form of a Bluetooth RS232 serial port adapter that is manufactured by BrainBoxes.

It will be appreciated that this type of Bluetooth arrangement provides a simple means for alerting the controller of the system 100 that an abnormality (error) exits with the system 100 and in particular, with the device 2000. Since Bluetooth communication is used as the means for communication, the remote device 2000 must be placed within the prescribed distance from the controller of the system 100 that contains the other Bluetooth component. Thus, the device 2000 can be at a remote location in the same room or it can even be placed in another room.

Since a number of different Bluetooth devices (e.g., bagger 2000) can be in communication with the single controller 100, the controller can monitor multiple peripheral devices at one time and easily distinguishes each device 2000 from one another so as to permit the detection of a malfunction at any of the devices 2000. Once the controller of the system 100 detects that a malfunction has occurred, the controller then determines which peripheral device 2000 sent the error signal and then based on the identification of the malfunctioning peripheral device 2000, the controller selects the proper remedial action to be taken in order to correct the situation. For example, if the controller receives an error signal from a peripheral device #1, the controller identifies that the peripheral device #1 is the syringe bagger machine and then can generate an error message directing the operator to the bagger machine and also can run other operation check procedures, such as checking to see if the supply of bags is empty, etc., and also can active remedial measures, such as stopping the feeding of the bags and/or stopping the peripheral device all together. If the error message is received from a peripheral device #2 (e.g., a label printer) proximate the bagger apparatus, then the controller takes remedial action, such as checking the supply of labels, etc.

It will also be appreciated that the Bluetooth components 2010, 2020 can be arranged so that upon the occurrence of a malfunction or other type of error at the peripheral device 2000, a controller associated with the peripheral device detects and diagnosis the source of the error and instructs the Bluetooth component 2020 to send a message to the other Bluetooth component 2010. In other words, the Bluetooth components 2010, 2020 can be constructed and configured so that an error message (signal) identifying the source of the error can be sent to the Bluetooth component 2010 and upon receiving the message at the component 2010, the master controller of the system 100 then reads and processes the message (signal) and then based on stored remedial information and instruction, the controller takes the necessary remedial action, e.g., alerting an operator as to the specific problem with peripheral device and/or taking active remedial action, such as replacement of an item t(bags, drug delivery devices, etc.) that have run out, and/or viewing a particular section for a jam or the like. In this embodiment, the Bluetooth communications network alerts the master controller not only that an error or malfunction exists but also it communicates to the master controller the type of error or malfunction that exists so that the master controller can take more detailed and specific remedial action. For example, if a sensor at the peripheral bagger device detects that the device has run out of a feed supply of bags (roll of bags), then the controller at the peripheral device generates an error message that is unique as to the observed malfunction (e.g., empty bag feed). The master controller receives this unique error message and then based on the type of error, the master controller undertakes appropriate remedial action, e.g., alerting the operator and/or causing a new feed of bags to be loaded into the peripheral device.

The use of a Bluetooth communications network permits not only error messages (signals) to be sent from a remote device but also permits other forms of communication between the remote device and the master controller of the system. One of the advantages, as mentioned above, with Bluetooth technology is that the communication between the peripheral device and the master controller is automatic and therefore, any number of different forms of communication can be utilized, including, sending information that relates to operation of the peripheral device.

It will be appreciated by persons skilled in the art that the present invention is not limited to the embodiments described thus far with reference to the accompanying drawings; rather the present invention is limited only by the following claims.

What is claimed is:

1. A method of operating an automated medication preparation system to prepare and deliver a prescribed dosage of medication to a drug delivery device comprising the steps of:
    inputting a drug order that contains instructions for forming the prescribed dosage of medication;
    providing a plurality of stations for receiving, handling and processing a drug delivery device so that the prescribed dosage of medication is delivered to the drug delivery device, wherein at least one of the stations includes a peripheral device for performing at least one operation;
    operating a transporting device that receives and holds more than one drug delivery device such that each drug delivery device moves in a controlled manner from one station to another station; communicating with the peripheral device by means of a Bluetooth communications network to monitor a status of the at least one operation performed at the peripheral device; and
    delivering, in an automated manner, the prescribed dosage of medication to the drug delivery device in conformity with the drug order.

2. An automated medication preparation system for preparing a prescribed dosage of medication in a drug delivery device comprising:

a plurality of stations for receiving, handling and processing the drug delivery device so that the prescribed dosage of medication is delivered to the drug delivery device, wherein at least one of the stations includes a peripheral device for performing at least one operation;

a transporting device that receives and holds more than one drug delivery device and moves the drug delivery devices in a controlled manner from one station to another station;

a master controller that tracks and controls the movement of the transporting device and operation of equipment at one or more stations; and a Bluetooth communications network between the peripheral device and the master controller such that the peripheral device automatically communicates with the controller when the peripheral device is within a predetermined distance from the controller, wherein the Bluetooth communications network includes a first Bluetooth component that is operatively coupled to the master controller and a second Bluetooth component that is operatively coupled to the peripheral device, the two Bluetooth components in automatic communication with one another;

wherein the system is configured so that two or more separate drug delivery devices are acted upon at the same time at two or more different stations.

3. The system of claim 2, wherein the peripheral device comprises an automated bagger machine that receives filled drug delivery devices and seals one or more in a bag structure.

4. The system of claim 2, wherein the controller includes software that provides a virtual communications port that sends an arbitrary signal to the second Bluetooth component and if a connection is established between the peripheral device and the master controller, the arbitrary signal is echoed back to the controller, thereby immediately indicating that the second Bluetooth component is operating, and wherein if the arbitrary signal is echoed back, second Bluetooth device is receiving no power, thereby indicating a malfunction at the peripheral device.

5. The system of claim 2, wherein the periphery device is configured so that when a malfunction results, power to the second Bluetooth component is cut off resulting in the first Bluetooth component not receiving a signal echo, thereby instructing the master controller of the occurrence of a malfunction at the peripheral device.

6. The system of claim 2, wherein the peripheral device comprises an automated bagger apparatus for bagging and sealing one more drug delivery devices and the controller is programmed to check the status of the Bluetooth communications network to see if all of the Bluetooth devices are powered up before placing the drug delivery device on a mechanism for delivering a filled drug delivery device from one station to the peripheral device and if a malfunction is detected, the drug delivery device is not delivered to the peripheral device.

7. The system of claim 2, wherein the peripheral device comprises a labeler device that is in wireless communication with the master controller by means of a first Bluetooth component that is operatively coupled to the master controller and a second Bluetooth component that is operatively coupled to the peripheral device, wherein the controller is alerted to a malfunction of the peripheral device and the master controller influences the operation on the drug delivery device by the peripheral device.

8. The system of claim 2, wherein the Bluetooth communications network includes a first Bluetooth component that is operatively coupled to the master controller and a second Bluetooth component that is operatively coupled to the peripheral device, the peripheral device having a local controller that is in communication with the second Bluetooth component and is configured to generate an error signal when a malfunction or error is observed at the peripheral device, the error signal uniquely identifying the type of error that is observed, the unique error signal being delivered to the second Bluetooth component and then wirelessly transmitted to the first Bluetooth component which delivers the error signal to the master controller which then takes one or more remedial actions.

9. The system of claim 2, wherein the master controller monitors a status of communication in the Bluetooth communications network prior to advancing the drug delivery device to the peripheral device and if there is a break in communication with the peripheral device, the master controller prevents delivery of the drug delivery device to the peripheral device and generates an error message.

10. The system of claim 2, wherein the second Bluetooth component is configured so that when the peripheral device has a change in its operating state or mode, communication between the first and second Bluetooth components is altered resulting in the master controller being alerted to this change at the peripheral device.

11. The system of claim 2, wherein the peripheral device is configured so that once it is reset, the first and second Bluetooth components communicate with one another in a normal operation mode that is indicative of the peripheral device being free of malfunction and operating in a normal mode.

12. An automated medication preparation system for preparing a prescribed dosage of medication in a drug delivery device comprising:

a plurality of stations for receiving, handling and processing the drug delivery device so that the prescribed dosage of medication is delivered to the drug delivery device, wherein at least one of the stations includes a peripheral device for performing at least one operation;

a transporting device that receives and holds more than one drug delivery device and moves the drug delivery devices in a controlled manner from one station to another station; a master controller that tracks and controls the movement of the transporting device and operation of equipment at one or more stations;

a Bluetooth communications network between the peripheral device and the master controller such that the peripheral device automatically communicates with the controller when the peripheral device is within a predetermined distance from the controller;

wherein the system is configured so that two or more separate drug delivery devices are acted upon at the same time at two or more different stations and wherein the transporting device comprises a cam-indexed device that receives and releasably holds each drug delivery device as it is controllably advanced from one station to a next station.

* * * * *